United States Patent
Roth et al.

(10) Patent No.: US 8,296,088 B2
(45) Date of Patent: Oct. 23, 2012

(54) SYSTEMS AND METHODS FOR PERFORMING MEASUREMENTS OF ONE OR MORE MATERIALS

(75) Inventors: Wayne D. Roth, Leander, TX (US); Charles J. Collins, Austin, TX (US); William R. Deicher, Austin, TX (US); Jarden E. Krager, Cedar Park, TX (US); Adam R. Schilffarth, Cedar Park, TX (US); Ross G. Johnson, Austin, TX (US); Colin D. Bozarth, Austin, TX (US); Victor Selvaraj, Austin, TX (US); Nicolas F. Arab, Austin, TX (US); Bruce J. C. Bernard, Austin, TX (US); Donald A. Conner, Pflugerville, TX (US); Robert S. Roach, Georgetown, TX (US)

(73) Assignee: Luminex Corporation, Austin, TX (US)

( * ) Notice: Subject to any disclaimer, the term of this patent is extended or adjusted under 35 U.S.C. 154(b) by 197 days.

(21) Appl. No.: 12/781,550

(22) Filed: May 17, 2010

(65) Prior Publication Data

US 2010/0228513 A1    Sep. 9, 2010

Related U.S. Application Data

(63) Continuation-in-part of application No. 11/757,841, filed on Jun. 4, 2007.

(60) Provisional application No. 60/803,781, filed on Jun. 2, 2006.

(51) Int. Cl.
*G01D 18/00* (2006.01)
*G01N 21/00* (2006.01)
*C12M 1/34* (2006.01)
*G01R 33/02* (2006.01)
*G01N 31/00* (2006.01)

(52) U.S. Cl. ............... 702/85; 702/94; 422/63; 422/67; 422/82.05; 436/55; 436/164; 436/165; 435/286.1; 435/286.2; 435/287.1; 435/288.7; 356/436; 356/441; 356/442; 324/259; 324/260

(58) Field of Classification Search ............... None
See application file for complete search history.

(56) References Cited

U.S. PATENT DOCUMENTS 4,326,851 A    4/1982    Bello et al.
(Continued)

FOREIGN PATENT DOCUMENTS

DE    102005027312    12/2006
(Continued)

OTHER PUBLICATIONS

Sandin et al., "Magnetophoresis and cytometry with magnetic microparticles," International Congress Series, vol. 1300, 2007, pp. 271-274.

(Continued)

*Primary Examiner* — Neil N Turk
(74) *Attorney, Agent, or Firm* — Fulbright & Jaworski L.L.P.

(57) ABSTRACT

Systems and methods for performing measurements of one or more materials are provided. One system is configured to transfer one or more materials to an imaging volume of a measurement device from one or more storage vessels. Another system is configured to image one or more materials in an imaging volume of a measurement device. An additional system is configured to substantially immobilize one or more materials in an imaging volume of a measurement device. A further system is configured to transfer one or more materials to an imaging volume of a measurement device from one or more storage vessels, to image the one or more materials in the imaging volume, to substantially immobilize the one or more materials in the imaging volume, or some combination thereof.

21 Claims, 19 Drawing Sheets

U.S. PATENT DOCUMENTS

| | | | |
|---|---|---|---|
| 4,817,652 | A | 4/1989 | Liu et al. |
| 5,016,027 | A | 5/1991 | Uebbing |
| 5,032,381 | A | 7/1991 | Bronstein et al. |
| 5,124,738 | A | 6/1992 | Yamashita |
| 5,493,922 | A | 2/1996 | Ramey et al. |
| 5,736,330 | A | 4/1998 | Fulton |
| 5,825,399 | A | 10/1998 | Orlicki et al. |
| 5,981,180 | A | 11/1999 | Chandler et al. |
| 6,057,107 | A | 5/2000 | Fulton |
| 6,139,800 | A | 10/2000 | Chandler |
| 6,165,795 | A | 12/2000 | Mize et al. |
| 6,210,203 | B1 | 4/2001 | Ma |
| 6,268,222 | B1 | 7/2001 | Chandler et al. |
| 6,449,562 | B1 | 9/2002 | Chandler et al. |
| 6,514,295 | B1 | 2/2003 | Chandler et al. |
| 6,524,793 | B1 | 2/2003 | Chandler et al. |
| 6,528,165 | B2 | 3/2003 | Chandler |
| 6,592,822 | B1 | 7/2003 | Chandler |
| 6,649,414 | B1 | 11/2003 | Chandler et al. |
| 6,899,810 | B1 | 5/2005 | Pitt et al. |
| 6,913,877 | B1 | 7/2005 | Chaplen et al. |
| 6,939,720 | B2 | 9/2005 | Chandler et al. |
| 7,384,561 | B2 | 6/2008 | Utsunomiya |
| 7,542,861 | B1 | 6/2009 | You et al. |
| 7,576,505 | B2 | 8/2009 | Chen |
| 2003/0082587 | A1 | 5/2003 | Seul et al. |
| 2003/0113714 | A1 | 6/2003 | Belcher |
| 2003/0186465 | A1 | 10/2003 | Kraus et al. |
| 2004/0234898 | A1* | 11/2004 | Batishko et al. .............. 430/312 |
| 2005/0003464 | A1 | 1/2005 | Tibbe et al. |
| 2005/0271557 | A1 | 12/2005 | Lee et al. |
| 2006/0105395 | A1 | 5/2006 | Pempsell |
| 2006/0263271 | A1 | 11/2006 | Sillman |
| 2007/0009395 | A1 | 1/2007 | Jiang |
| 2007/0025887 | A1 | 2/2007 | Baeuerle et al. |
| 2007/0064990 | A1 | 3/2007 | Roth |
| 2008/0198448 | A1 | 8/2008 | Ganser et al. |
| 2008/0277477 | A1 | 11/2008 | Thuries et al. |
| 2008/0277480 | A1 | 11/2008 | Thuries et al. |
| 2009/0310213 | A1 | 12/2009 | Hing et al. |

FOREIGN PATENT DOCUMENTS

| | | |
|---|---|---|
| EP | 0410645 | 1/1991 |
| EP | 1394270 | 3/2004 |
| WO | 91/09141 | 6/1991 |
| WO | 96/37313 | 11/1996 |
| WO | 97/20214 | 6/1997 |
| WO | 2005/073695 | 8/2005 |
| WO | 2006/079016 | 7/2006 |
| WO | 2006/133899 | 12/2006 |

OTHER PUBLICATIONS

International Search Report, PCT/US2007/070345, mailed Dec. 14, 2007.

* cited by examiner

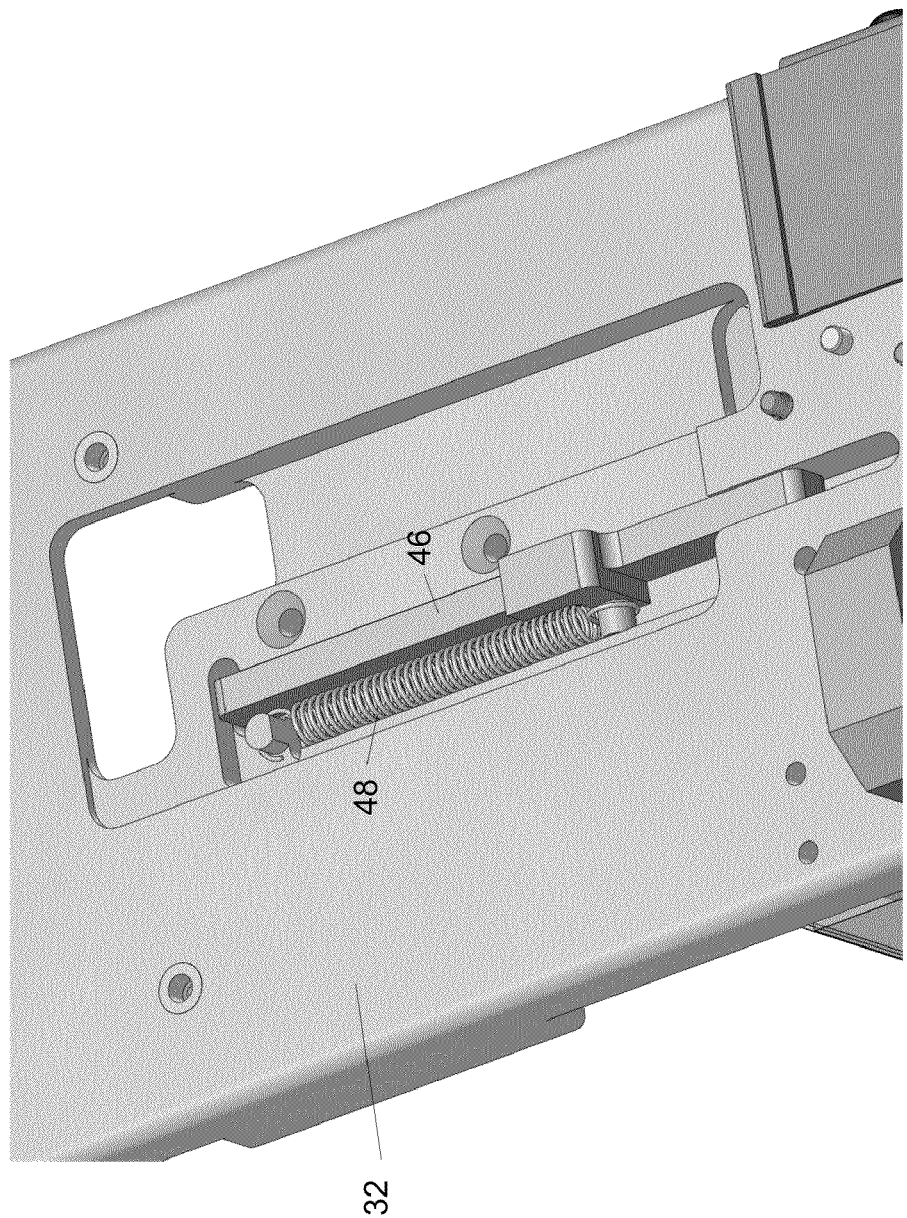

SYSTEMS AND METHODS FOR PERFORMING MEASUREMENTS OF ONE OR MORE MATERIALS

BACKGROUND OF THE INVENTION

1. Field of the Invention

This invention generally relates to systems and methods for performing measurements of one or more materials. In particular, the invention relates to a system and method configured to transfer one or more materials to an imaging volume of a measurement device from one or more storage vessels, to image the one or more materials in the imaging volume, to substantially immobilize the one or more materials in the imaging volume, or some combination thereof.

2. Description of the Related Art

The following descriptions and examples are not admitted to be prior art by virtue of their inclusion within this section.

Instrumentation typically employed in flow cytometry provide viable systems for measuring one or more characteristics of (or "interrogating") internally dyed microspheres (or other particles) to which are coupled fluorescent dyes, fluorophores, or fluorescent tags. The fluorescent dyes, fluorophores, or fluorescent tags coupled to the microspheres may indicate and/or be approximately proportional to a biological reaction that has taken place at the surface of the microspheres. Examples of such instrumentation are described in U.S. Pat. No. 5,981,180 to Chandler et al., which is incorporated by reference as if fully set forth herein. The Luminex 100 line of instruments, which are commercially available from Luminex Corporation, Austin, Tex., essentially are flow cytometers capable of achieving substantially high sensitivity and specificity.

Flow cytometers typically include several relatively sophisticated and expensive devices such as semiconductor lasers, precision syringe pumps, photomultiplier tubes (PMT), and avalanche photo diodes. While performance of such systems is substantially high, the cost of the instruments can be prohibitive for some markets. Additionally, flow cytometers are physically large, heavy and relatively fragile, and typically a trained technician must be on hand at the installation site to perform alignment of the flow cytometers. Flow cytometers also utilize relatively large volumes of sheath fluid to hydrodynamically focus the particle stream into a relatively narrow core.

Imaging using detectors such as charged coupled device (CCD) detectors are employed in several currently available instruments used in biotechnology applications. Many of the commercially available systems are configured to image target human (or other animal) cells. Such systems are not utilized to generate images using different wavelengths of light for determining the identity of the cells or subset to which the cells belong. For multiplexed applications in which CCD detectors are used to measure fluorescent emission of cells, the subset or class of cells or other particles is based on the absolute position of the fluorescence emission within the image rather than the characteristics of the fluorescence emission such as wavelength composition.

Accordingly, it would be desirable to develop systems and methods for performing measurements of one or more materials that are less expensive than currently used systems, that have less complex optical configurations that are more mechanically stable than currently used systems thereby making shipping and installation of the systems easier, that are smaller than currently used systems, that are more sensitive than currently used systems, that have shorter acquisition times and higher throughput than currently used systems, that utilize fewer consumables such as sheath fluid than currently used systems, that enable a final wash of the one or more materials for which the measurements are to be performed, or some combination thereof.

SUMMARY OF THE INVENTION

The problems outlined above are largely addressed by the system and methods of the present invention. The system is configured to perform imaging and analysis of particles to measure characteristics of the particles. The system is configured to transfer particles to an imaging chamber, immobilize the particles on an imaging plane and take an image of the particles. The system includes a fluid handling subsystem for loading and removing samples from the device and for cleaning the device or samples. An optics subsystem includes an illumination configuration, such as a plurality of LED's and a collection configuration, such as one or more imaging sensors. Finally, an immobilization subsystem is employed to hold the sample during the measurement interval. In a preferred form, the immobilization subsystem includes a magnet and the sample includes magnetic beads where the magnet can be selectively operated to immobilize the magnetic beads during imaging. In another form, the position of the collection configuration and the illumination configuration in relation to the sample during imaging is optimized.

BRIEF DESCRIPTION OF THE DRAWINGS

Other objects and advantages of the invention will become apparent upon reading the following detailed description and upon reference to the accompanying drawings in which:

FIG. 2c illustrates an underside view of the storage vessel platform and well plate retention device illustrated in FIGS. 2a and 2b;

Figure 1:
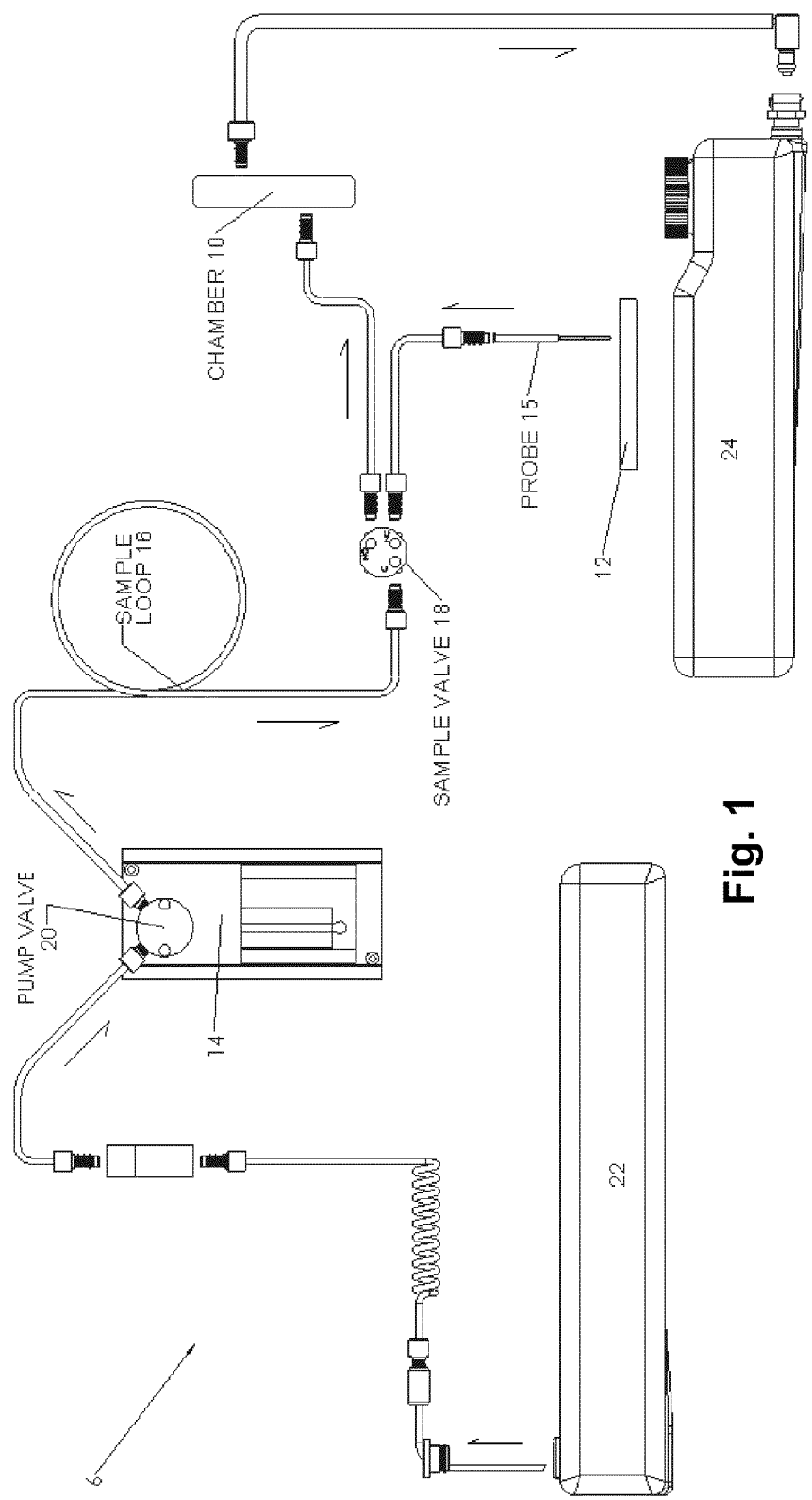
FIG. 1 is a schematic diagram of a fluid handling subsystem of an imaging system.

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents and alternatives falling within the spirit and scope of the present invention as defined by the appended claims.

DETAILED DESCRIPTION OF THE PREFERRED EMBODIMENTS

Although some embodiments are described herein with respect to particles, beads, and microspheres, it is to be understood that all of the systems and methods described herein may be used with particles, microspheres, polystyrene beads, microparticles, gold nanoparticles, quantum dots, nanodots, nanoparticles, nanoshells, beads, microbeads, latex particles, latex beads, fluorescent beads, fluorescent particles, colored particles, colored beads, tissue, cells, micro-organisms, organic matter, non-organic matter, or any other discrete substances known in the art. The particles may serve as vehicles for molecular reactions. Examples of appropriate particles are illustrated in U.S. Pat. Nos. 5,736,330 to Fulton, 5,981,180 to Chandler et al., 6,057,107 to Fulton, 6,268,222 to Chandler et al., 6,449,562 to Chandler et al., 6,514,295 to Chandler et al., 6,524,793 to Chandler et al., and 6,528,165 to Chandler, which are incorporated by reference as if fully set forth herein. The systems and methods described herein may be used with any of the particles described in these patents. In addition, particles for use in method and system embodiments described herein may be obtained from manufacturers such as Luminex Corporation, Austin, Tex. The terms "particles," "microspheres," and "beads" are used interchangeably herein.

In addition, the types of particles that are compatible with the systems and methods described herein include particles with fluorescent materials attached to, or associated with, the surface of the particles. These types of particles, in which fluorescent dyes or fluorescent particles are coupled directly to the surface of the particles in order to provide the classification fluorescence (i.e., fluorescence emission measured and used for determining an identity of a particle or the subset to which a particle belongs), are illustrated in U.S. Pat. Nos. 6,268,222 to Chandler et al. and 6,649,414 to Chandler et al., which are incorporated by reference as if fully set forth herein. The types of particles that can be used in the methods and systems described herein also include particles having one or more fluorochromes or fluorescent dyes incorporated into the core of the particles. Particles that can be used in the methods and systems described herein further include particles that in of themselves will exhibit one or more fluorescent signals upon exposure to one or more appropriate light sources. Furthermore, particles may be manufactured such that upon excitation the particles exhibit multiple fluorescent signals, each of which may be used separately or in combination to determine an identity of the particles.

The embodiments described herein are capable of achieving substantially equivalent or better performance than that of a flow cytometer, while overcoming the issues described in the section above entitled "Description of the Related Art." The embodiments described herein include several configurations using two broad based imaging methods. For fluorescence detection or collection, a single sensor such as a photomultiplier tube (PMT) or avalanche photodiode (APD) per detected wavelength may be employed as commonly used in flow cytometers. However, the particularly preferred embodiments envision a one- or two-dimensional charge coupled device (CCD) or another suitable array detector for fluorescence detection. The excitation source may be configured to provide widespread illumination (i.e., illumination provided over a relatively large area of the imaging volume of the measurement device (such as the entire imaging volume of the measurement device) simultaneously) using light emitted by light sources such as light emitting diodes (LEDs) and delivered to one or more materials in the imaging volume of the measurement device directly or via fiber optics. Alternatively, the excitation source may be configured to provide illumination of a relatively small spot in the imaging volume of the measurement device, and the system may be configured to scan the relatively small spot across the imaging volume. In this manner, the illumination may be configured as a relatively "tiny flying spot" of focused light generated from one or more LED's, one or more lasers, one or more other suitable light sources, or some combination thereof.

The embodiments described herein also provide a number of advantages over other systems and methods for performing measurements of one or more materials. For example, the embodiments described herein are advantageously less expensive than other systems and methods. In particular, in several configurations described herein, the embodiments may include a relatively inexpensive CCD as a photon detector rather than a PMT, relatively simple LEDs in place of lasers, a relatively inexpensive pump in place of a precision syringe pump to move fluids, or some combination thereof. Thus, the aggregate cost of the embodiments described herein can be reduced by approximately an order of magnitude. In addition, the embodiments described herein are advantageous due to a substantially simpler optical configuration than that typically used for flow cytometry thereby rendering the embodiments described herein substantially mechanically stable. Such mechanical stability enables shipping the system embodiments described herein via a standard shipping service (e.g., a UPS-type service). Furthermore, such mechanical stability allows the system embodiments described herein to be installed by a user who may or may not be a technically adept service person. Moreover, the embodiments described herein are advantageous since the system embodiments can be substantially small (e.g., conceivably the size of a pocket camera).

Another advantage of the embodiments described herein is that the embodiments provide the ability to integrate photons over a time period much longer than a few microseconds as is typical using a laser-based flow cytometer type system. Therefore, the embodiments described herein are capable of detecting particles with fewer molecules of fluorescence on the surface or otherwise coupled thereto than currently used systems and methods. As such, the embodiments described herein may advantageously have a higher sensitivity than other currently used systems and methods. In addition, the embodiments described herein may have substantially shorter measurement acquisition times and therefore higher throughput than currently used systems. For example, in embodiments configured to use a CCD/LED "flood-illumination" configuration, acquisition of sample measurements is faster since an entire sample or an entire population of particles can be measured in two or three images or "pictures," rather than serially particle by particle. In another example, for users that desire a relatively high throughput solution, a CCD/LED based system provides a comparatively inexpensive system, and in several instances, can be operated in parallel to quickly process a single microtiter plate or other sample.

Yet another advantage of the embodiments described herein is that sheath fluid is not used to hydrodynamically focus the particles as in flow cytometry. Still another advantage of the embodiments described herein is that a final "wash" of the one or more materials for which measurements are to be performed is possible within the system to remove free fluorochromes or other materials that will interfere with the measurements from the liquid surrounding the particles thereby lowering the background light detected by the measurement device (e.g., by the imaging sensors of the measurement device).

The description of the embodiments provided further herein is generally divided into three subsections, in which different system embodiments are described. For example, one subsection relates to fluidic configurations that may be included in the system embodiments described herein. The fluid handling configurations can be used to introduce or transfer the one or more materials (e.g., beads and/or other reagents after one or more reactions have been allowed to take place on the surface of the beads) to an imaging volume of the measurement device from one or more storage vessels. Another subsection relates to optical configurations that may be included in the system embodiments described herein. In general, the optical configurations may include different combinations of excitation sources and photon detectors, sometimes referred to herein as illumination subsystems and photosensitive detection subsystems, respectively. An additional subsection relates to particle immobilization configurations and methods that may be included in, or used by, the system embodiments described herein. The systems described herein may include such particle immobilization configurations since in an imaging system the particles preferably do not move substantially during the measurement interval. Note that any combination of the system configurations described in the subsections above may be combined to produce a final imaging system embodiment.

As set forth in more detail below, a number of methods and routines are provided which relate to the system subsections described herein. In general, the methods are automated and thus, are implemented through a computer and more specifically by program instructions which are executable by a computer processor. Thus, the imaging system described herein includes program instructions which are executable by a processor for performing automated routines, particularly the methods described in reference to FIGS. 3, 7, 10, 11, 12, and 14. The program instructions may be transmitted over or stored on a storage medium. The storage medium may include but is not limited to a read-only memory, a random access memory, a magnetic or optical disk, or a magnetic tape. It is noted that the imaging system described herein may, in some cases, be configured to perform processes other than those specifically described herein and, therefore, the computer-implemented methods and program instructions of systems described herein are not necessarily limited to the depiction of FIGS. 3, 7, 10, 11, 12, and 14.

Turning now to the drawings, it is noted that the figures are not drawn to scale. In particular, the scale of some of the elements of the figures is greatly exaggerated to emphasize characteristics of the elements. It is also noted that the figures are not drawn to the same scale. Elements shown in more than one figure that may be similarly configured have been indicated using the same reference numerals.

Figure 6:
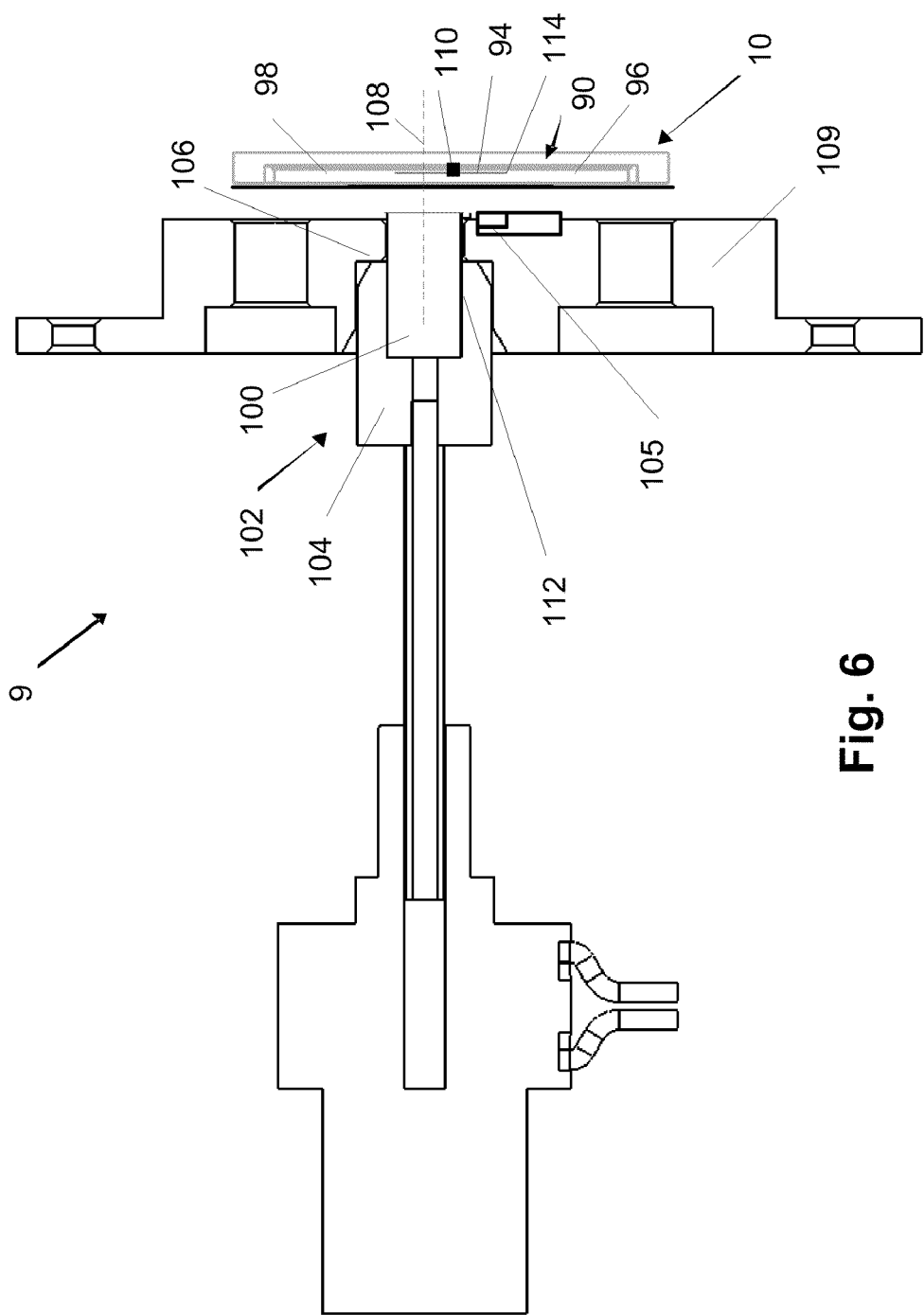
FIG. 6 illustrates a cross-sectional view of an immobilization subsystem of an imaging system.
Figure 8:
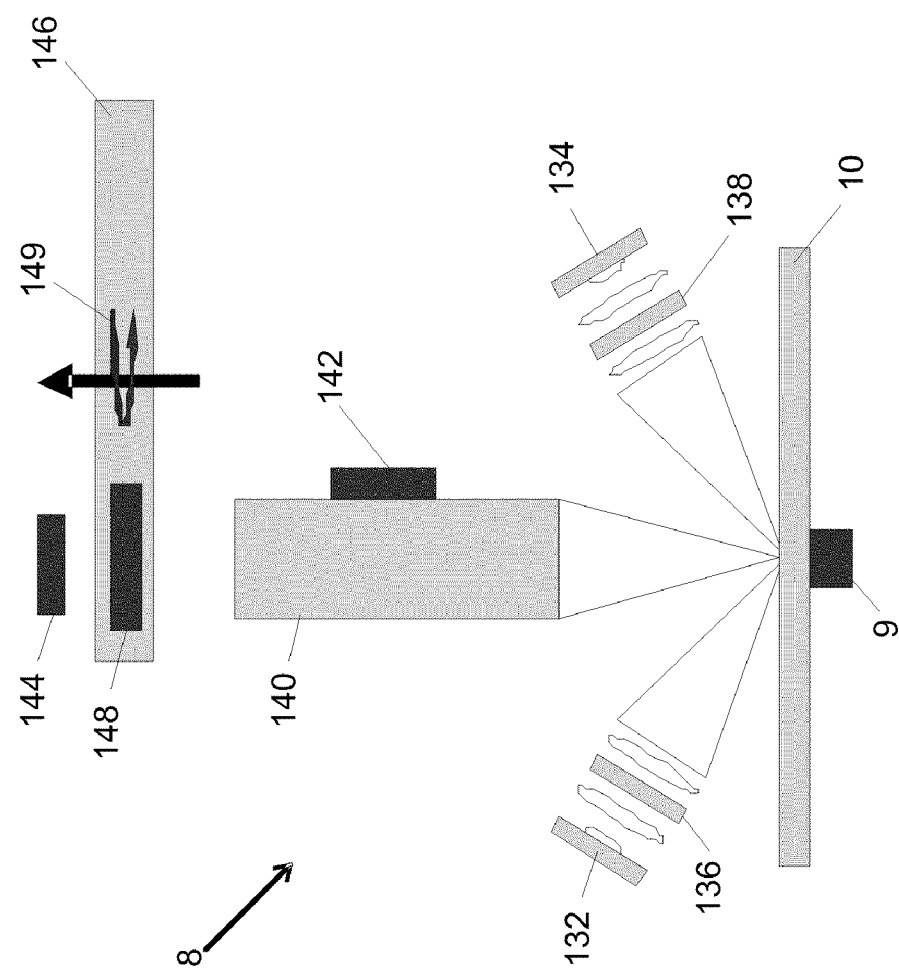
FIG. 8 is a schematic diagram of an optics subsystem of an imaging system.

FIGS. 1, 6, and 8 are illustrative of exemplary embodiments of subsystems which may be combined in a system for analyzing a fluidic assay. In particular, FIG. 1 illustrates functional components of fluid handling subsystem 6. FIG. 6 illustrates components of immobilization subsystem 9 and FIG. 8 illustrates functional components of optic subsystem 8. It is noted that the configurations of fluid handling subsystem 6, particle immobilization subsystem 9 and optic subsystem 8 are not necessarily limited to the depictions of FIGS. 1, 6 and 8. In particular, fluid handling subsystem 6, particle immobilization subsystem 9 and optic subsystem 8 may include additional or different components and/or may have components arranged in a different manner than depicted in FIGS. 1, 6 and 8. Thus, FIGS. 1, 6 and 8 illustrate mere examples of fluid handling subsystem 6, particle immobilization subsystem 9, and optic subsystem 8 and FIGS. 1, 6 and 8 should not necessarily restrict the system described herein.

Fluid handling subsystem 6 is generally configured to transfer one or more materials to an imaging region of a fluidic flow-through chamber from one or more storage vessels. As shown in FIG. 1, samples may be transferred into the imaging system from sample storage vessel 12 by sample collection probe 15. By way of bi-directional pump 14, pump valve 20, sample loop 16, and sample valve 18, fluid handling subsystem 6 may route the collected sample to fluidic flow-through chamber 10. In particular, bi-directional pump 14 may draw a sample collected by sample probe 15 into sample loop 16 and later expel fluid from the sample loop into chamber 10. Sample loop 16 refers to a length of tubing between pump 14 and sample valve 18, which serves as a reservoir for the collected sample. The tubing may have any suitable configuration. In addition, bi-directional pump 14 may include any suitable pump known in the art.

The function of sample valve 18 is to connect sample probe 15 to sample loop 16 when aspirating the sample from sample storage vessel 12 and to connect sample loop 16 to chamber 10 when dispensing the sample into the chamber. Pump valve 20 is utilized at the pump end of sample loop 16 to introduce solution/s (e.g., a drive solution or a wash solution) from storage vessel 22 into sample loop 16. Additional storage vessels may be included in the system for introducing solutions into sample loop 16 and, thus, the system is not limited to the inclusion of storage vessel 22. In other cases, storage vessel 22 may be omitted from the system. In any case, pump valve 20 and sample valve 18 may include any suitable valves known in the art. In some embodiments, the system includes program instructions executable by a processor for automating the withdrawal of a sample from sample storage vessel 12 into sample loop 16. In addition or alternatively, the system may include program instructions executable by a processor for loading the sample into chamber 10 from sample loop 16. In any case, the system may generally be configured to dispense a solution from fluidic flow-through chamber 10 after analysis and, in some embodiments, the system may include container 24 for collection of the dispensed solution.

As noted above, samples may be transferred into the system from sample storage vessel 12 by sample probe 15. Sample storage vessel 12 may be configured as any suitable assay sample container known in the art, such as a micro titer plate for example. In general, the system described herein and particularly in relation to FIGS. 1-3 may include a storage vessel platform configured to receive and secure a sample storage vessel containing an assay. More specifically, the system described herein may include a storage vessel platform which is configured to prevent movement of sample storage vessel 12 during operations of the system, particularly when sample probe 15 is used retrieve samples therefrom. In conventional assay analysis systems, a sample storage vessel is often supported upon a storage vessel platform, but the vessel is generally not secured to prevent movement. Due to friction between a sample probe and a pierceable cover overlying a storage vessel, sample storage vessels may become dislodged by the action of the sample collection probe piercing the cover to retrieve the sample and retracting from the sample storage vessel. The system described herein, however, includes a storage vessel platform configured to combat such a problem as discussed in more detail below in reference to FIGS. 2a-2f.

Figure 2A:
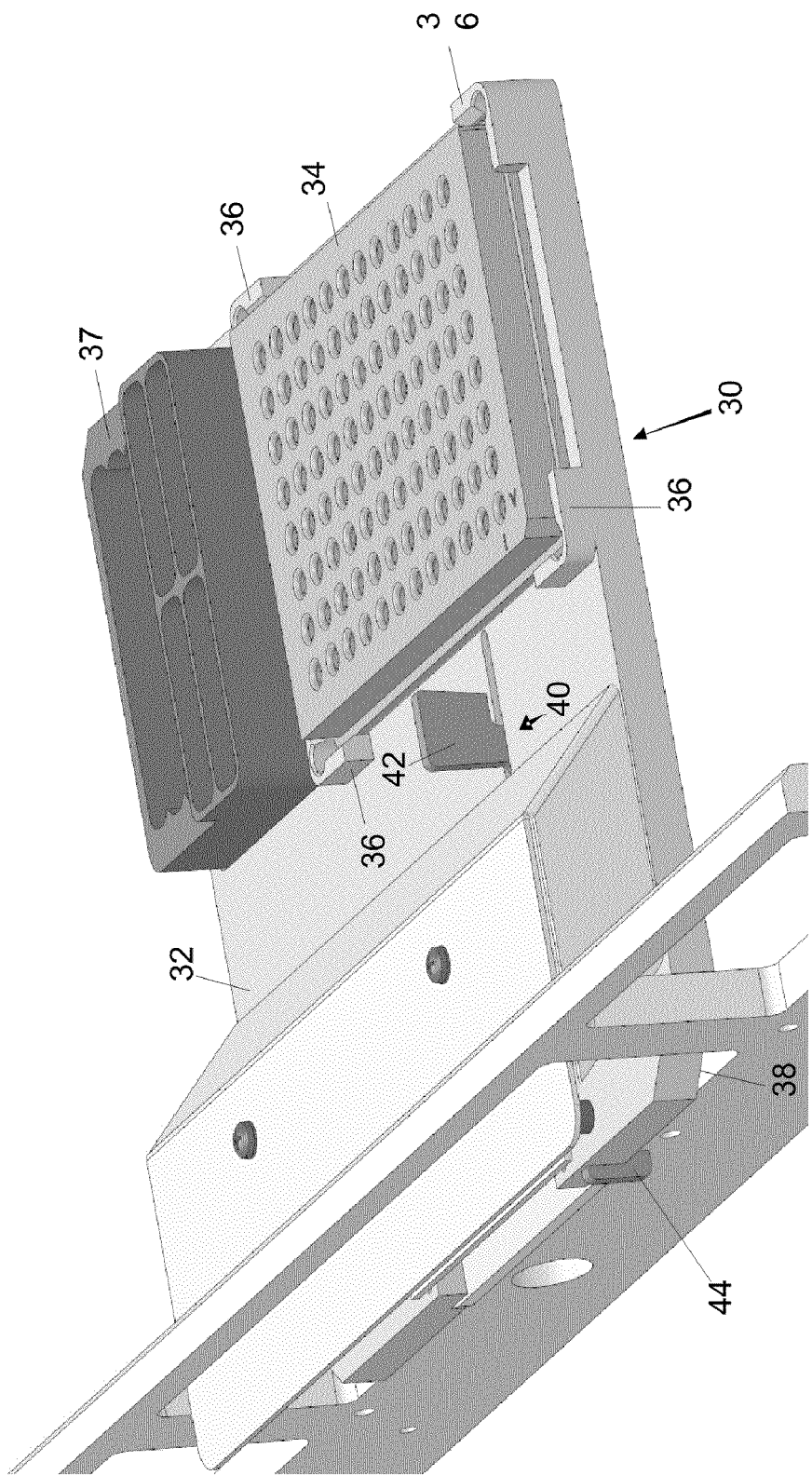
FIG. 2a illustrates a perspective view of a storage vessel platform in an extracted position having a sample storage vessel received therein with a well plate retention device spaced apart from the sample storage vessel.
Figure 2B:
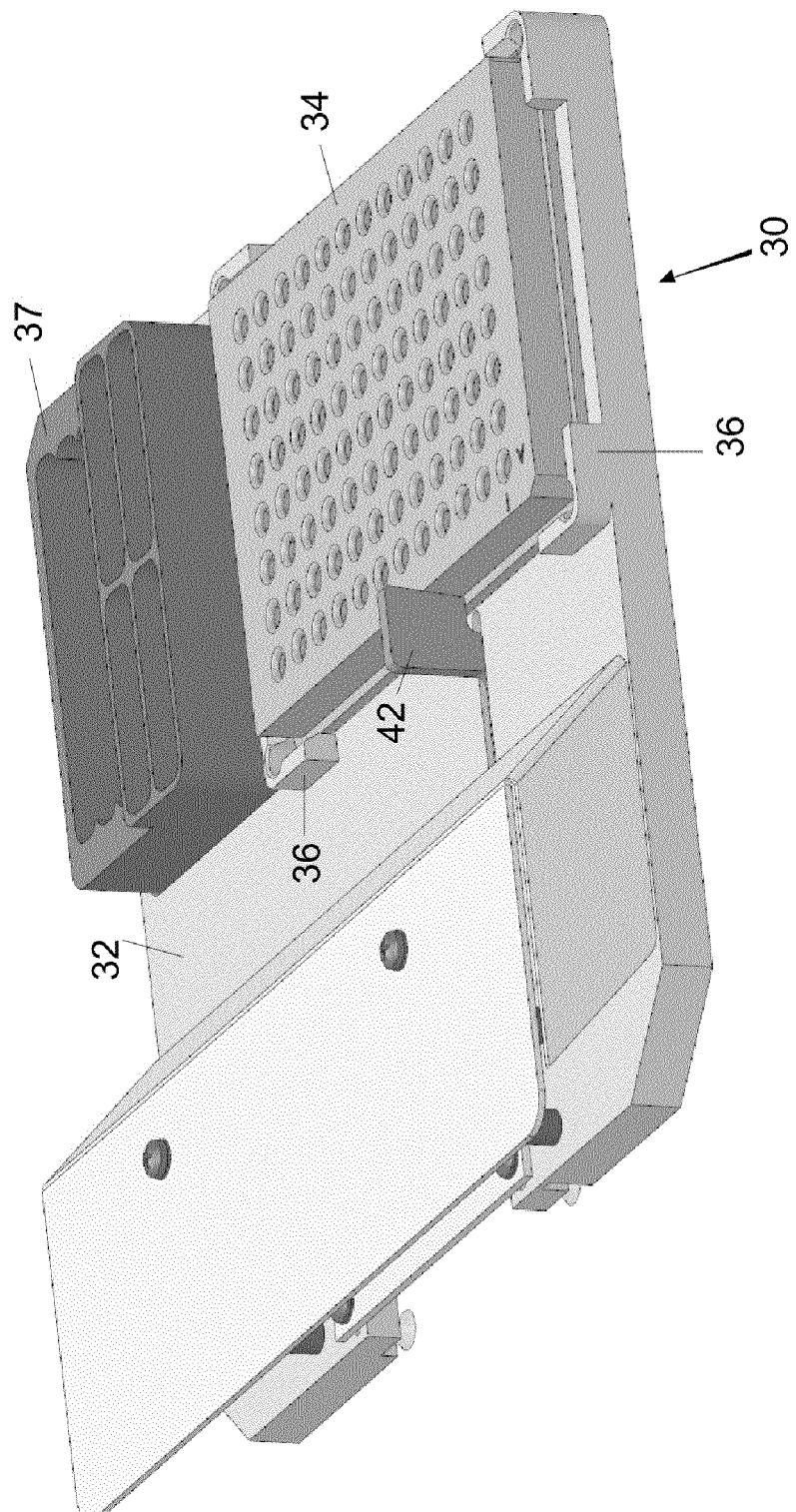
FIG. 2b illustrates a perspective view of the storage vessel platform depicted in FIG. 2a in a retracting position having the sample storage vessel received therein and secured by the well plate retention device.

Turning to FIGS. 2a and 2b, an exemplary configuration of a storage vessel platform is shown which is configured for receiving and securing a sample storage vessel. In particular, storage vessel platform 30 is shown in FIGS. 2a and 2b having support base 32 with a partially framed area for accommodating storage vessel 34. Storage vessel platform 30 includes locating features 36 extending from support base 32 demarcating the partially framed area and spring-loaded pushbar 40 integrated within support base 32. Fluid reservoir 37 is provided adjacent to the partially framed area and is generally configured to store maintenance fluids for the assay samples held in storage vessel 34. In accompaniment with storage vessel platform 30, the system includes a mechanism for extracting and retracting the storage vessel platform within the system, specifically in and out of opening 38 of the system's casing. The mechanism may include any suitable configuration known in the art. For example, in some cases, the mechanism may resemble a configuration used for conventional compact disc players.

As set forth in more detail below, the configuration of storage vessel platform 30 to secure storage vessel 34 within the partially framed area of support base 32 includes a particular design and placement of spring-loaded pushbar 40 to apply force upon a sidewall of storage vessel 34 when storage vessel platform 30 is retracted within the system. In order to allow storage vessel 34 to be removed from the system, spring-loaded pushbar 40 is also configured to release the applied force when storage vessel platform 30 is being extracted out of the system. Such configurations of spring-loaded pushbar 40 include the designs of portions 42 and 44 as well as the design and position of spring 48 (depicted in FIG. 2c), all of which are described in more detail below in reference to FIGS. 2a-2f.

In addition to the design and placement of spring-loaded push bar 40, the configuration of storage vessel platform 30 to secure storage vessel 34 within the partially framed area of support base 32 includes at least a portion of the interior surfaces of locating features 36 having a roughened surface. In particular, a roughened surface on an interior surface of locating features 36 (i.e., a surface facing inward to the partially framed area of support base 32) may generally offer sufficient friction to secure a corresponding sidewall of storage vessel 34 when spring-loaded push bar 40 applies a force on a sidewall of storage vessel 34. Any one or more of locating features 36 may include a roughened surface on their interior surfaces. In some cases, however, it may be particularly advantageous to have roughened interior surfaces on locating features which contact a sidewall of storage vessel 34 opposing the sidewall to which spring-loaded push bar 40 applies a force. Such an embodiment may be advantageous for securing storage vessel 34 along at least one direction of the partially framed area of support base 32.

Although FIGS. 2a and 2b illustrate locating features 36 at the corners of the partially framed area of support base 32, the configuration, number, and position of locating features 36 is not necessarily so limited. In particular, storage vessel platform 30 may include any number and size of locating features for demarcating the area to receive storage vessel 34 as long at least an opening is provided for spring-loaded pushbar 40 to apply a force upon a sidewall of storage vessel 34 when the storage vessel platform is retracted within the system. As such, storage vessel platform 30 may include additional locating features, locating features at different positions and/or locating features of alternative configurations framing the area for receiving storage vessel 34. For instance, storage vessel platform 30 may include a locating feature which extends along an entire side portion of the area for receiving storage vessel 34 and, in some cases, may include a locating feature which extends along three sides of the area for receiving storage vessel 34 and possibly a portion of the side to which spring-loaded pushbar 40 will be actuated. Alternatively, storage vessel platform 30 may include one or more separate locating features arranged along the side portions of the receiving area for storage vessel 34, i.e., with or without locating features positioned at the corners of the area for receiving storage vessel 34. In any case, it is noted that the partially framed area of support base 32 is not restricted to accommodating 96-well microtiter plates as depicted for storage vessel 34 in FIGS. 2a and 2b. In particular, the partially framed area of support base 32 may be configured to accommodate storage vessels of any size and may generally vary depending on the specifications of the system.

Correlating the configuration of spring-loaded pushbar 40 and interior surface/s of locating features 36 to secure storage vessel 34 within storage vessel platform 30, the spring-loaded pushbar is generally configured to apply a force large enough to secure a sidewall of the storage vessel against the roughened surface/s of the locating features, but low enough such that storage vessel 34 is not deformed. In some cases, the force applied by spring-loaded pushbar 40 may be configured in conjunction with the coefficient of friction provided by the roughened surface/s of locating features 36 to specifically override friction forces between a sample probe and a cover overlying storage vessel 34. Configurations of spring-loaded pushbar 40 for applying such forces are described in more detail below in reference to FIGS. 2d-2f. In general, the friction force between a sample probe and a cover overlying storage vessel 34 may vary among systems and process runs due to variations in system design and the weight of storage vessels and covers. During the development of the storage vessel platform described herein, the friction force between a sample probe and a cover overlying storage vessel 34 was estimated to be approximately 18 grams or less and, thus, the configurations described below are generally designed to override such a friction force. It is noted, however, that the configurations noted below may be suitable for overriding greater friction forces or may be modified to do so.

An exemplary range of a spring force found suitable during the development of the storage vessel platform described herein was between approximately 0.8 lbs and approximately 1.0 lbs, but larger or smaller forces may be considered depending on the design specifications of the system. The configurations of the roughened surface/s of locating features 36 to provide a certain minimum coefficient of friction may include the degree of roughness as well as the roughness profile, both of which may vary depending on design specifications of the system (e.g., the size of locating features 36, the area the roughened surface, the size of the storage vessel, etc.). An exemplary minimum coefficient of friction found suitable during the development of the storage vessel platform described herein was approximately 0.12, but larger or smaller coefficients may be considered. In addition, a knurled surface was found to be suitable for the storage vessel platform described herein and, in some cases, a sawtooth knurled surface having teeth angled downward proved to be particularly advantageous for a securing a storage vessel therein.

In addition to the configurations of spring-loaded pushbar 40 to apply a particular force and the roughened surface of locating features 36 to provide a minimum coefficient of friction, the materials of spring-loaded pushbar 40 and locating features 36 may aid in securing storage vessel 34 within storage vessel platform 30 as well as aid in maintaining the operation of spring-loaded pushbar 40. In general, spring-loaded pushbar 40 and locating features 36 may includes materials which are resistant to corrosion and deformation. Exemplary materials include metals, such as aluminum and stainless steel, and self-lubricating materials, such as polyoxymethylene. In some cases, self-lubricating materials may be particularly beneficial for reducing galling of spring-loaded pushbar 40. Polyoxymethylene is commercially available from DuPont company under the trade name Delrin.

FIGS. 2a-2c illustrate an exemplary design and position of spring-loaded pushbar 40 to apply force upon a first sidewall of the storage vessel when storage vessel platform 30 is retracted within the system and further to release the applied force when storage vessel platform 30 is being extracted out of the system. In particular, FIG. 2a illustrates storage vessel platform 30 in an extracted position, specifically in that portion 42 of spring-loaded pushbar 40 is spaced apart from storage vessel 34 and portion 44 of spring-loaded pushbar 40 is against a sidewall of the casing framing opening 38. In such cases, spring-loaded pushbar 40 is not applying a force upon storage vessel 34 and, therefore, the storage vessel is not secured within storage vessel platform 30. Such a scenario may be applicable when storage vessel 34 is being loaded or unloaded from storage vessel platform 30. The operation of the storage vessel platform for either scenario includes portion 44 of spring-loaded pushbar 40 catching the edge of window 38, halting the movement of spring-loaded pushbar 40 while the rest of the storage vessel platform moves to the final extraction position. In this manner, portion 44 affects a spacing between spring-loaded pushbar 40 and the partially framed area for receiving storage vessel 34. In some embodiments, the spacing may be of sufficient clearance such that a mechanical arm may effectively load and unload storage vessel 34 to/from the area without hindrance.

FIG. 2b illustrates storage vessel platform 30 in a partially or fully retracted position, specifically in that portion 42 of spring-loaded pushbar 40 is applying a force upon a sidewall of a storage vessel 34 sufficient to secure an opposing sidewall of storage vessel 34 against corresponding local features 36. Although not illustrated in FIG. 2b, it is noted that portion 44 of spring-loaded pushbar 40 is not against the sidewall of the casing framing opening 38 when storage vessel platform 30 is in a partially or fully retracted position. Such a scenario may be applicable when storage vessel platform 30 is being retracted into the system for sampling or when storage vessel platform 30 is being extracted from the system but prior to portion 44 of spring-loaded pushbar 40 catching the edge of opening 38.

FIG. 2c illustrates storage vessel platform 30 from an underside view, denoting the integration of spring-loaded pushbar 40 within support base 32. In particular, from such a view, it is shown that spring-loaded pushbar 40 includes beam 46 and spring 48 connecting the beam to support base 32. Beam 46 may generally connect portions 42 and 44 of spring-loaded pushbar 40. Spring 48 may include a compression or a tension spring. In some cases, it may be advantageous to employ a tension spring to avoid the buckling of the spring during operation. Although not shown in FIG. 2c, storage vessel platform 30 may include an underside shield covering beam 46 and/or spring 48. In some embodiments, the underside shield may include a pushbar stop to halt the movement of spring-loaded pushbar 40 when storage vessel platform 30 is being retracted into the system and no storage vessel is arranged on the platform. The objective of the pushbar stop is to prevent portion 42 of spring-loaded pushbar 40 from contacting the end of the slot in which portion 42 moves when no storage vessel is arranged on storage vessel platform 30.

Portion 42 of spring-loaded push bar 40 may include a number of configurations to aid in the application of force upon a sidewall of storage vessel 34 when storage vessel platform 30 is retracted within the system. For instance, in some cases, portion 42 of spring-loaded pushbar 40 may have a roughened surface for contacting the sidewall of storage vessel 34. In such cases, the roughened surface of portion 42 may be configured to provide a minimum coefficient of friction in conjunction with the coefficient of friction provided by the roughened surface/s of locating features 36 as well as the force provided by spring 48 to override friction forces between a sample probe and a cover overlying storage vessel 34. The degree of roughness as well as the roughness profile delineating the coefficient of friction of the roughened surface on portion 42 may vary depending on design specifications of the system. In some embodiments, the roughened surface on portion 42 may include a degree of roughness and/or a roughness profile similar to those described above for the roughened surface/s of locating features 36. Such characteristics are not reiterated for the sake of brevity.

An additional or alternative configuration to aid in the application of force upon a sidewall of storage vessel 34 when storage vessel platform 30 is retracted within the system is for portion 42 of spring-loaded push bar 40 to have an angled face for exerting an angled downward force upon the sidewall of the storage vessel. In general, portion 42 may be configured to contact any point along the sidewall of storage vessel 34 to apply the angled downward force. In some embodiments, however, it may be particularly advantageous to configure portion 42 such that contact is made at a corner point of storage vessel 34. In particular, such a configuration may generally apply a greater downward force upon the storage vessel for a given force applied by spring 48 relative to contacting a non-corner point along the vertical sidewall of the storage vessel. The corner contact point may be the top portion of the storage vessel or, alternatively, may be the corner point of a bottom flange of the storage vessel. Storage vessels used for holding assays often include a bottom flange outlining the bottom portion of the vessel. In fact, the American National Standards Institute (ANSI) has identified three standardized heights of bottom-outside flanges for microplates in ANSI document ANSI/SBS 3-2004: a short flange height of 2.41 mm+/−0.38 mm, a medium flange height of 6.10 mm+/−0.38 mm, and a tall flange height of 7.62 mm+/−0.38 mm.

Figure 2D:
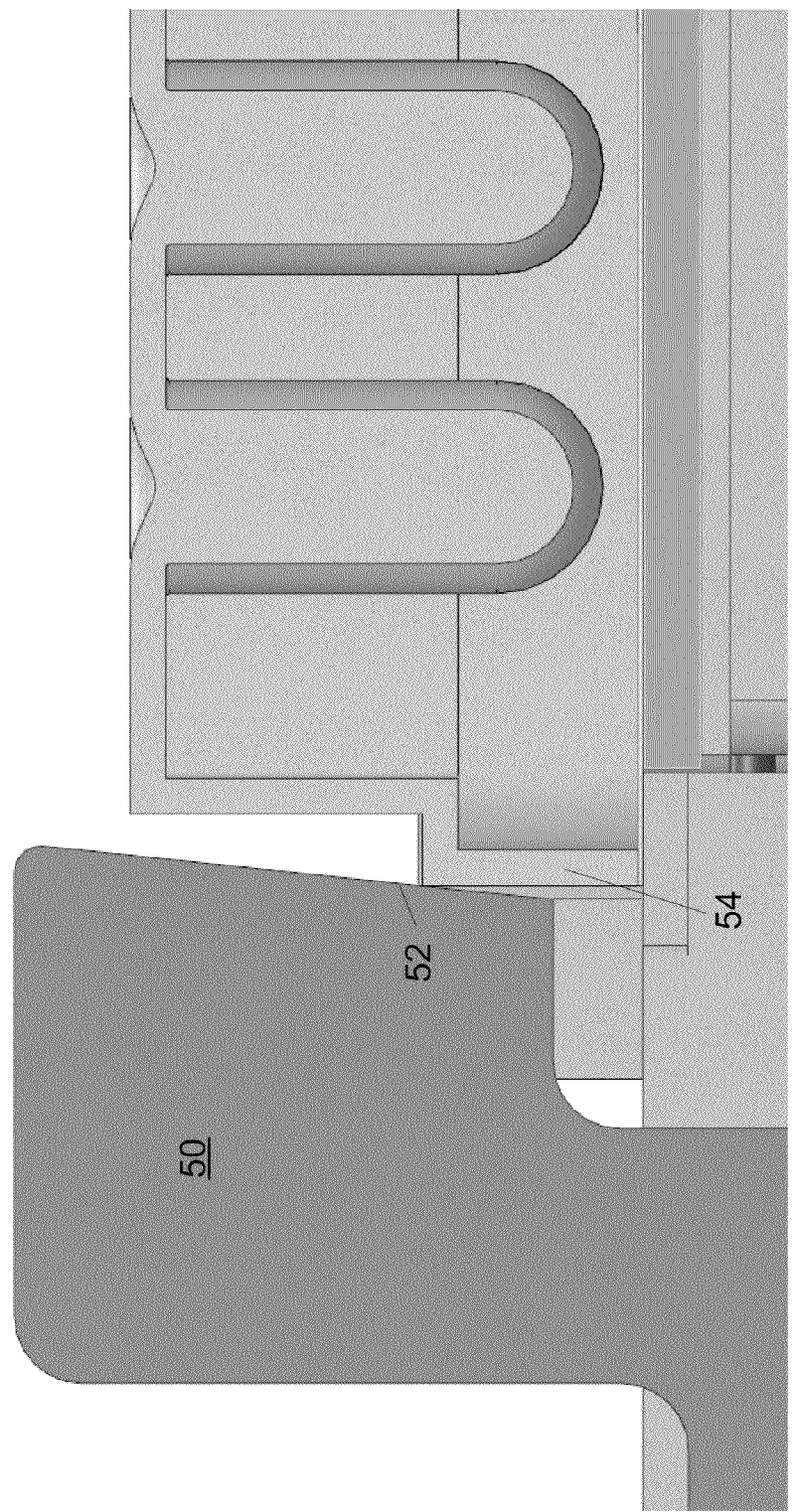
FIGS. 2d-2f illustrate different configurations of spring-loaded pushbars for well plate retention devices.
Figure 2E:
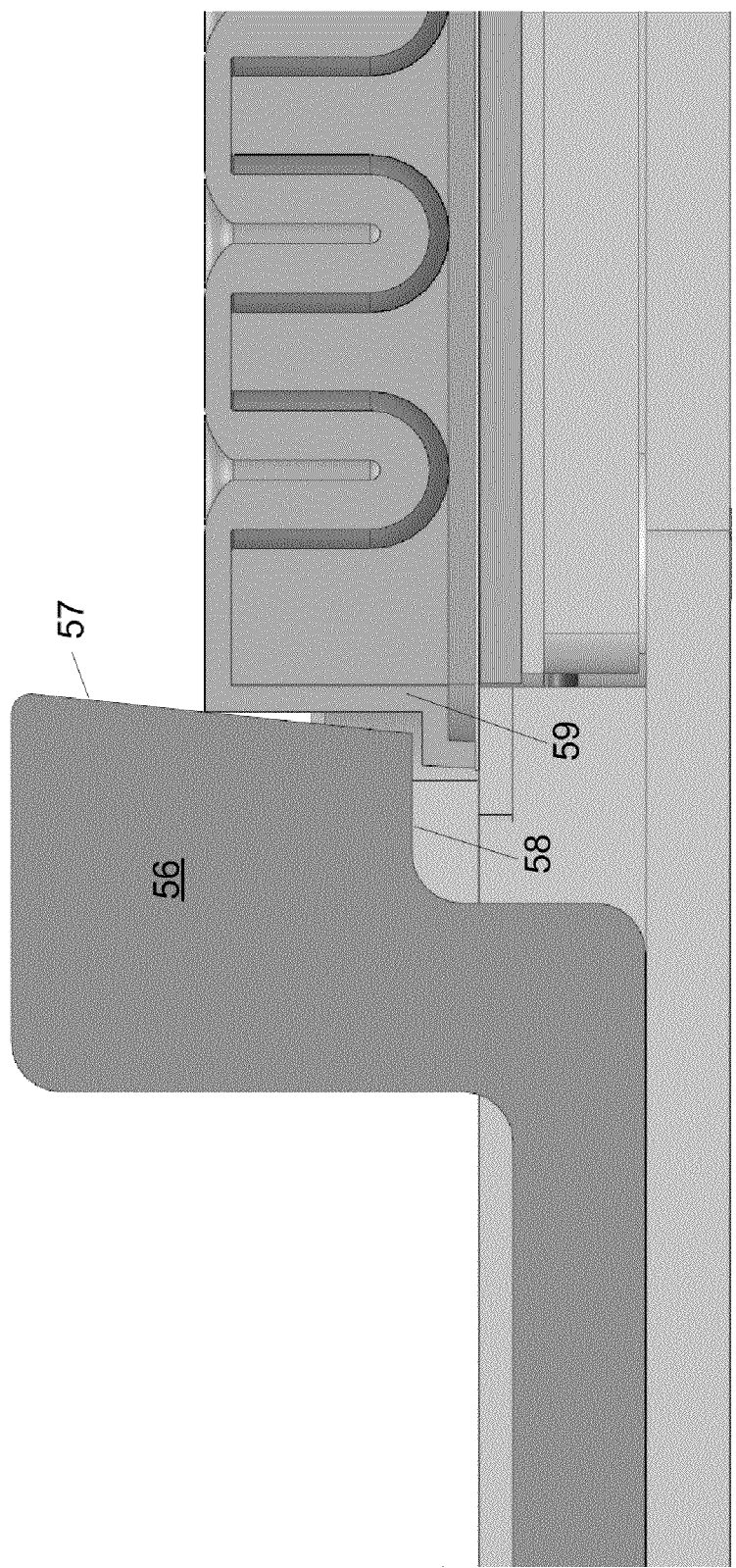
Figure 2F:
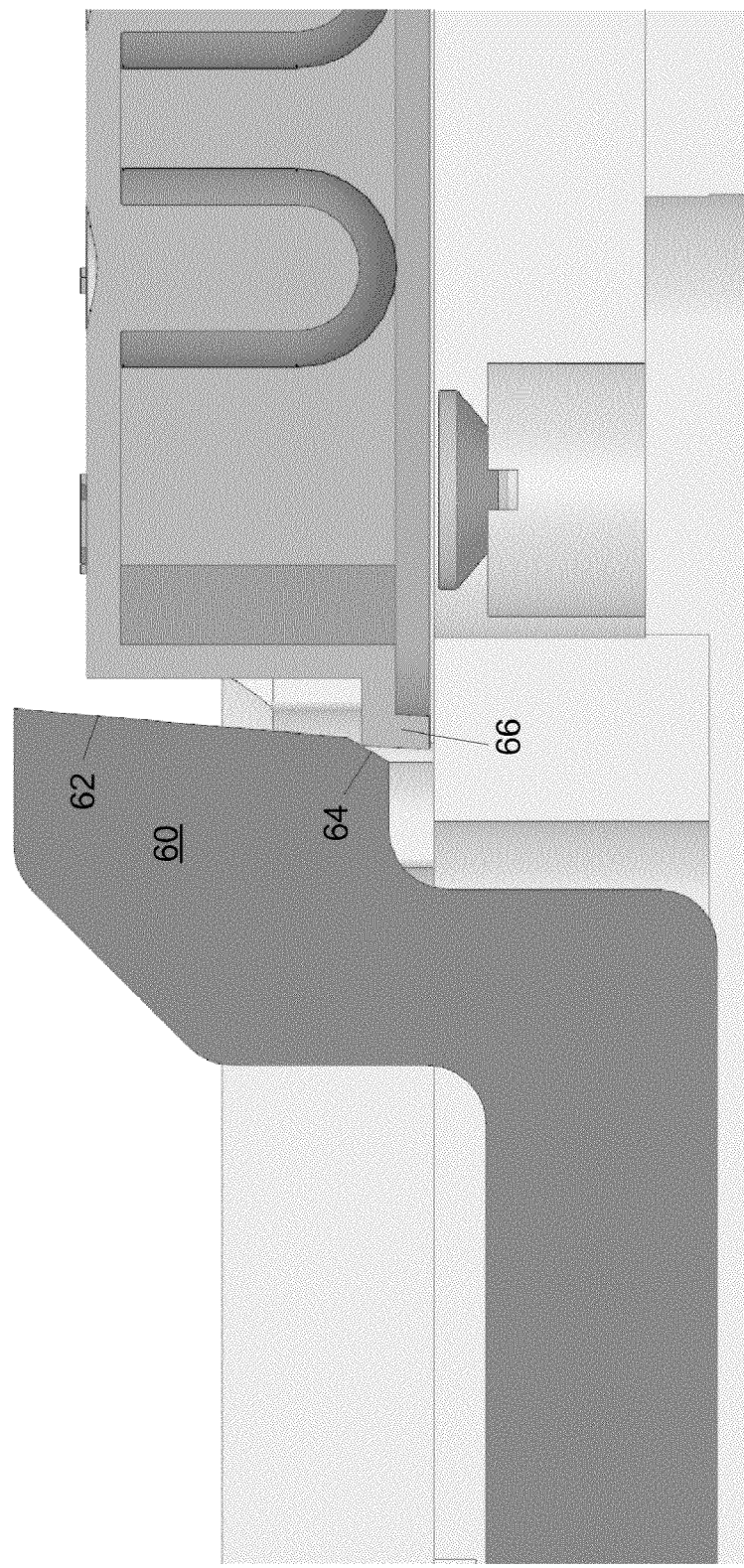

In general, it would be advantageous to design portion 42 to accommodate different configurations of storage vessels including those of having bottom flanges of different heights as well as storage vessels in which the sidewalls above the bottom flanges vary in height and/or angle. Height variations of bottom flanges and storage vessels as a whole as well as variations of angles of bottom flanges and sidewalls of storage vessels, however, present a challenge to try to effectuate contact at a corner point of a storage vessel. Furthermore, the option to include a heater plate below a storage vessel on a storage vessel platform further exacerbates the problem. Exemplary configurations which address such an issue are illustrated in FIGS. 2d-2f. In particular, FIGS. 2d-2f illustrate different configurations of portion 42 of spring-loaded push bar 40 that generally effectuate contact at corner points of various configurations of storage vessels, particularly those that follow ANSI standards for microplates.

For instance, FIG. 2d illustrates configuration 50 having angled face 52 for applying a downward angled force upon a sidewall of storage vessel 54 placed in a storage vessel platform. In general, angled face 52 is dimensioned such that configuration 50 contacts a corner point of storage vessel 54. In some cases, angled face 52 may contact a corner point of the bottom flange of storage vessel 54 as shown in FIG. 2d. In other embodiments, angled face 52 may contact a corner point of the upper portion of the storage vessel (i.e., the portion of storage vessel 54 above the bottom flange), such as shown in FIG. 2e for configuration 56. It is noted that FIG. 2e may denote different configurations of portion 42 of spring-loaded push bar 40. In particular, FIG. 2e may be used to denote a configuration when portion 42 is applied to storage vessels having bottom flanges of relatively short heights. Alternatively, FIG. 2e may be used to denote a configuration specifically dimensioned to have a bottom face which clears bottom flanges of most storage vessels as described in more detail below.

The adaptation of configuration 50 to contact a corner point of a bottom flange of a storage vessel may be particularly applicable to storage vessels having medium flange heights (e.g., 6.10 mm+/−0.38 mm per ANSI document ANSI/SBS 3-2004) and tall flange heights (e.g., 7.62 mm+/−0.38 mm per ANSI document ANSI/SBS 3-2004). In contrast, adaptation of configuration 50 to contact a corner point of an upper portion of a storage vessel may be particularly applicable to storage vessels having short flange heights (e.g., 2.41 mm+/−0.38 mm per ANSI document ANSI/SBS 3-2004). In any case, in order to effectuate such contact points with storage vessels having different sized bottom flanges, the angle of angled face 52 relative to a vertical axis of configuration 50 may be less than or equal to approximately 10.0 degrees and, in some cases, less than or equal to approximately 7.0 degrees and, in further cases, less than or equal to approximately 5.0 degrees. Larger angles, however, may be considered.

An alternative configuration for portion 42 of spring-loaded push bar 40 may be to dimension portion 42 to clear a bottom flange of a storage vessel such that contact may be specifically made with a top corner of the storage vessel. An exemplary depiction of such an embodiment is illustrated in FIG. 2e in which angled face 57 contacts the top corner of storage vessel 59. As noted above, FIG. 2e may denote different configurations of portion 42 of spring-loaded push bar 40. In particular, FIG. 2e may be used to denote a configuration which is described above in reference to FIG. 2d when it is applied to storage vessels having bottom flanges of relatively short heights. In such configurations, configuration 56 in FIG. 2e may be dimensioned such that bottom face 58 clears the top surface of the storage vessel platform in which it resides (e.g., by approximately 1 or 2 mm). Alternatively, FIG. 2e may be used to denote a configuration specifically dimensioned to have a bottom face which clears bottom flanges of storage vessels such that angled face 57 may consistently contact top corners of storage vessels rather than corner points of bottom flanges of storage vessels.

In order to effectuate the latter configuration for microplates which follow ANSI standards, configuration 56 may be dimensioned such that bottom face 58 is arranged at least 3.0 mm above the upper surface of the storage vessel platform and, in some cases, at least 7.0 mm above the upper surface of the storage vessel platform, and yet other embodiments, at least 8.5 mm above the upper surface of the storage vessel platform. In some cases, configuration 56 may be dimensioned such that bottom face 58 is arranged to clear a bottom flange of a storage vessel when it is arranged upon a heater plate. An exemplary dimension for such an embodiment may involve bottom face 58 arranged at least 13.0 mm above the upper surface of the storage vessel platform. In any of such cases, angled face 57 may be of an angle as described for angled face 52 for FIG. 2d. In particular, the angle of angled face 57 relative to a vertical axis of configuration 56 may be less than or equal to approximately 10.0 degrees and, in some cases, less than or equal to approximately 7.0 degrees and, in further cases, less than or equal to approximately 5.0 degrees. Larger angles, however, may be considered.

Another alternative configuration for portion 42 of spring-loaded pushbar 40 may be in the form of configuration 60 illustrated in FIG. 2f. As shown in FIG. 2f, configuration 60 includes chamfered face 64 at the lower edge of angled face 62. Chamfered face 64 is at a greater angle than angled face 62 relative to a vertical axis of configuration 60. As a consequence, chamfered face 64 may effectuate a greater downward force upon storage vessel 66 than angled face 62 for a given spring force of spring-loaded pushbar 40. Chamfered face 64 may be dimensioned such that configuration 60 contacts a corner point of the bottom flange of storage vessel 66 as shown in FIG. 2f. The angle of chamfered face 64 relative to a vertical axis of configuration 60 may vary depending on design specifications of the system, but an exemplary range may be between approximately 5 degrees and approximately 45 degrees.

It is noted that the height of portion 42 of spring-loaded pushbar 40 relative to storage vessel 34 may generally be dimensioned to insure it fits within opening 38 such that storage vessel platform 30 may be extracted and retracted within the system. In some embodiments, the height of portion 42 of spring-loaded pushbar 40 may need to be further restricted, particularly if the spring-loaded pushbar is arranged beneath another component of the platform. In particular, storage vessel platform 30 may be alternatively configured such that spring-loaded pushbar 40 is arranged beneath fluid reservoir 37 and, thus, in such situations the height of portion 42 of spring-loaded pushbar 40 may be particularly limited. In some cases, arranging spring-loaded pushbar 40 beneath fluid reservoir 37 may be advantageous to prevent contamination of the slot in which portion 42 of spring-loaded pushbar 40 moves.

Figure 3:
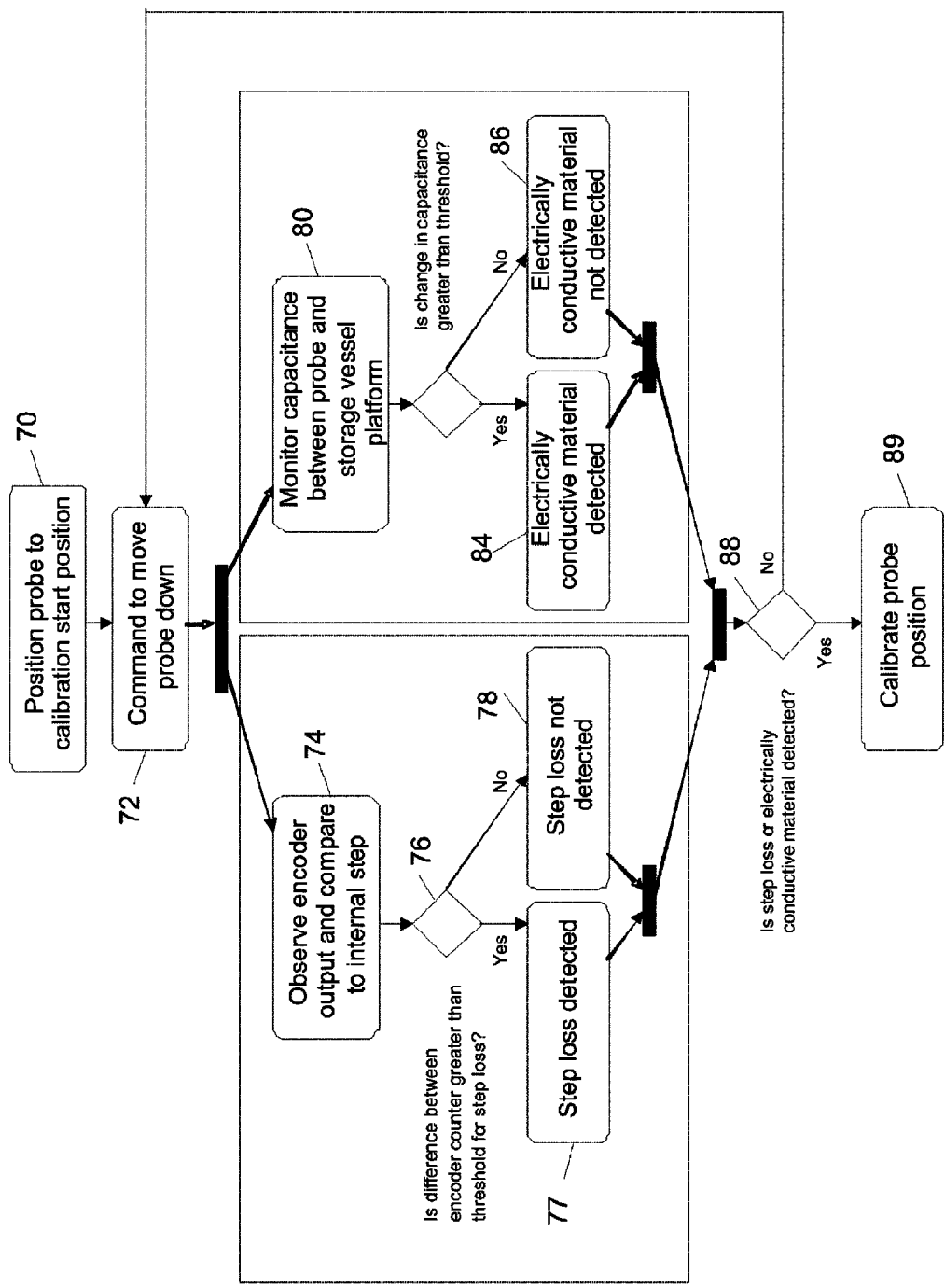
FIG. 3 illustrates a flowchart of a method for calibrating a position of a sample probe relative to a storage well of a storage vessel arranged upon a storage vessel platform.

As noted above, it is generally advantageous for a storage vessel platform of the imaging system described herein to accommodate storage vessels of different configurations. Such an accommodation may lead to other components of the imaging system to be adaptable as well. For example, various microtiter plates have wells of varying depth. In order to insure samples are adequately aspirated from wells of various storage vessels without causing damage to the storage vessels or the sample probe, it would be advantageous to be able to position the sample probe at different vertical positions relative to different storage vessels. Accordingly, the imaging system described herein may include an automated system for calibrating a position of a sample probe relative to a well of a storage vessel arranged in a storage vessel platform. More specifically, the imaging system described herein may include program instructions executable by a processor for such a procedure. In general, the program instructions are configured to identify a reference position within a storage vessel well and designate a target vertical position of a sampling probe relative to the identified reference position through operation of a suitable calibration routine. An exemplary calibration routine is depicted in FIG. 3 and is described in more detail below. It is noted that the calibration routine considered for the imaging system described herein may include additional and/or alternative procedures relative to those illustrated in FIG. 3 and, thus, the calibration routine described herein for determining sample probe position should not necessarily be restricted to the depiction of FIG. 3.

As shown in FIG. 3, a calibration routine for determining sample probe position may include block 70 in which a sample probe is positioned at a calibration start position relative to a storage vessel platform of the imaging system and, more specifically, relative to a well of a storage vessel arranged on the storage vessel platform. The process may involve moving the sample probe and/or the storage vessel platform. The calibration start position may be any x-y position of the sample storage vessel or storage vessel platform and is generally a predetermined position. In some cases, the calibration start position may be dependent on the type of storage vessel arranged in the system. In further or alternative embodiments, the calibration start position may be determined using alignment markers on the storage vessel and/or the storage vessel platform. In any case, a motor coupled to the sample probe is commanded to move from the calibration start position a set number of steps to drive the sample probe down toward a well of the storage vessel as denoted in block 72. The motor may be commanded to move any number of steps, including a single step or multiple steps, depending on the specifications of the system and the desired precision for identifying a reference position within the storage vessel well. Subsequent to and/or while the motor is commanded to move, the calibration routine may include one or two manners for monitoring the position of the sample probe relative to the storage vessel well. In particular, the calibration routine may include monitoring step loss of the motor as described in more detail below in reference to blocks 74-78 of FIG. 3 and/or may include monitoring capacitance between the sample probe and the storage vessel platform as described in more detail below in reference to blocks 80-86 of FIG. 3.

As shown in block 74, the step loss detection process includes monitoring the number of discrete steps the motor is commanded to move versus feedback from an encoder connected to the motor which measures actual physical movement of the motor. Using such a comparison, a determination is made at block 76 as to whether the difference between the preset number and the feedback from the encoder is greater than a predetermined threshold. The predetermined threshold may be any number of steps, including a single step or multiple steps, depending on the specifications of the system and the desired precision for identifying a reference position within the storage vessel well. As shown in blocks 77 and 78, respectively, step loss is detected if the difference between the preset number and the feedback from the encoder is greater than the predetermined threshold and, conversely, step loss is not detected when the difference is less than the predetermined threshold.

Detection of step loss is generally indicative that the sample probe cannot be driven further due to abutment with a hard stop, such as a bottom of a well or a hard object placed in the well. Such a process is generally suitable for storage vessels having wells made of relatively durable materials (e.g., rigid polymer materials), but can pose a problem for storage vessels having wells made of relatively fragile materials (e.g., filter paper materials). In particular, a step loss detection process is susceptible to damaging or deforming a well made of a relatively fragile material due to the motor continuing to drive the sample probe after contact with the bottom of the well or contact with a hard object placed in the well. More specifically, the sample probe may stretch the material of the well, thin the material of the well, poke through the well, and/or cause the well material to rupture when being driven by the motor during a step loss detection process. As such, it is sometimes advantageous to avoid a step loss detection process when working with storage vessels having wells made of relatively fragile materials.

An alternative manner for determining sample probe position which may avert damage to storage vessels having wells made of relatively fragile materials is to monitor the capacitance between the sample probe and the storage vessel platform and remove the drive current applied to the motor upon detection of a capacitance which is indicative of a position of the sample probe spaced apart from the bottom of the well. In general, the capacitance will increase as the sample probe is drawn closer to the storage vessel platform. As such, a threshold may be set which is indicative of a desired reference location within the well (e.g., a location spaced apart from the bottom of the well). Such a threshold may be the point at which the drive current applied to the motor is terminated such that the probe may be prevented from damaging the well. A disadvantage of such a process, however, is that capacitance increase is generally gradual and may be minute in magnitude since the surface area of the sample probe tip (i.e., the point of the sample probe closest to the storage vessel platform) may be relatively small. Sensors configured to accurately detect such capacitance may be expensive and/or may not be feasible and, thus, such a detection process may not be practical for systems which are configured for sample aspiration.

In order to obviate such a problem, a modified version of the method may include placing an electrically conductive material in the well of the storage vessel prior to the storage vessel being placed in the storage vessel platform. After the storage vessel is placed in the storage vessel platform, capacitance between the sample probe and the storage vessel platform may be monitored to detect contact of the sample probe with the electrically conductive material. In particular, placing an electrically conductive material within the well may advantageously provide a point within the well which upon contact with the sample probe increases the conductive area associated with the sample probe, causing a significant and immediate increase in capacitance between the sample probe and the storage vessel platform. Upon detection of this dramatic increase in capacitance, the drive current applied to the motor may be terminated and, thus, a known position of the sample probe within the well may be established without damaging the well. It is noted that it is the spacing above the well bottom that the electrically conductive material provides as well as the dramatic increase in capacitance that prevents the well from being damaged during such a process. In particular, the spacing provided by the electrically conductive material prevents the sample probe from puncturing the bottom of the well and the dramatic increase in capacitance offers a point at which to quickly terminate the drive current such that the sample probe does not continue to push on the electrically conductive material and damage the well.

In general, the electrically conductive material may be of a solid or fluidic form. For example, in some embodiments, the electrically conductive material may include an electrically conductive fluid, such as salt water for instance. An electrically conductive fluid may be advantageous for preventing deformation of the well since penetration of the sample probe through the fluid but above the well bottom will not cause the well to deform. A disadvantage of using an electrically conductive fluid, however, is the risk of contamination of the sample probe, well, and possibly other wells of the storage vessel, depending on the fluid used. As such, in alternative embodiments, an electrically conductive solid material may be used, including rigid materials and inherently malleable materials. The risk of contamination of other wells of the storage vessel is lessened when using an electrically conductive solid material, but solid materials may be more susceptible to deforming a well, particularly if the drive current applied to the sample probe is not terminated immediately upon contact with the solid material. Materials which are inherently malleable (e.g., gels) may lessen concerns regarding deformation since the materials may deform as a sample probe drives downward rather than transferring that pressure to the well. The selection of the type of electrically conductive material used may depend on a number of issues, including but not limited to the material and construction of the well of the storage vessel, and, thus, may vary among applications.

An example of a process of monitoring capacitance to detect an electrically conductive material placed within a well of a storage vessel is shown in blocks 80-86 of FIG. 3. It is noted that such a process is exemplary and additional or alternative steps may be utilized for such a process. As shown in block 80, the process includes monitoring the capacitance between the sample probe and the storage vessel platform via a capacitance sensor coupled between the sample probe and the storage vessel platform. In some cases, the monitoring process denoted in block 80 may involve monitoring and/or measuring capacitance directly. In other embodiments, however, the process of monitoring of capacitance denoted in block 80 may involve monitoring and/or measuring a characteristic which is proportional to capacitance, such as but not limited to current, voltage, or frequency. In the latter of such cases, the system may generally include an analog-to-digital converter which measures the characteristic corresponding to the capacitance (e.g., current, voltage, or frequency).

In general, the point of reference on the sample probe and the storage vessel platform for monitoring the capacitance may include any electrically conductive feature on those components, including those which are fixedly attached or removable from the sample probe and the storage vessel platform. For example, in some embodiments, a storage vessel platform may in some cases be equipped with an electrically conductive heater and, thus, the heater may serve as a point of reference for the capacitance measurement in some embodiments. Alternatively, a support base of the storage vessel platform may serve as a point of reference for the capacitance measurement. In any case, the capacitance may be monitored during or subsequent to the sample probe moving. In some cases, the capacitance may be monitored continuously, but in other cases, the capacitance may be monitored intermittently, such as after the motor moves a predetermined number of steps, including a single step or multiple steps.

Referring back to FIG. 3, after monitoring the capacitance between the sample probe and the storage vessel platform, the process continues to block 82 in which a determination is made as to whether a change in capacitance greater than a predetermined threshold has been detected. The predetermined threshold referred to in block 82 may generally be selected depending on the specifications of the system and the desired precision for identifying a reference position within the storage vessel well, and, thus, may vary among systems. As noted above in reference to block 80, monitoring the capacitance between the sample probe and the storage vessel platform may include monitoring any output signal from a given capacitance detector that is proportional to capacitance, such as but not limited to current, voltage, or frequency. In such cases, the determination made in block 82 is whether a change in the output signal is greater than a predetermined threshold. It is noted that the capacitance detector may be configured to translate capacitance to a correlating characteristic in a normal or inverse sense. For example, a capacitance detector may indicate decreases in voltage as capacitance increases since voltage is inversely related to capacitance. In alternative embodiments, however, the capacitance detector may output voltage signals which are directly proportional to changes in capacitance.

In any case, referring to blocks 84 and 86, respectively, an electrically conductive material placed in the well is detected if the predetermined threshold is crossed and, conversely, the electrically conductive material is not detected when the predetermined threshold is not crossed. As set forth above, contact with the electrically conductive material within the well is detected by a sudden increase in capacitance (or a sudden change in an output signal, such as voltage, from the capacitance detector) between the sample probe and storage vessel platform. At such a point, the motor may be terminated to prevent damage to the storage vessel by further lowering of the probe.

As noted above, the imaging system described herein is preferably configured to accommodate storage vessels of different configurations, including storage vessels having different types of materials for the wells. Although the methods described above of monitoring capacitance to determine a position of a sample probe within a well may be particularly suitable for storage vessels having wells made of fragile materials, the methods may be used with storage vessels having wells made of rigid materials. As such, the capacitance monitoring method may accommodate storage vessels having wells of different materials. Consequently, in some cases, the capacitance monitoring method may alone be used to calibrate a position of a sample probe relative to a well of a storage vessel. However, a disadvantage of the methods described above of monitoring capacitance is the time and handling of placing the electrically conductive material within the well of the storage vessel. In particular, it is generally advantageous to skip such a step if possible, particularly when storage vessels having wells made of rigid material are used.

An alternative to exclusively utilizing the capacitance monitoring method to calibrate a position of a sample probe relative to a well of a storage vessel is to utilize both the step loss detection method and the capacitance monitoring method for calibrating the sample probe position. In particular, the imaging system described herein may, in some embodiments, include program instructions executable by a processor for both monitoring capacitance between the sample probe and the storage vessel platform during or subsequent to the sample probe moving as well as monitoring the number of steps the motor moves the sample probe versus the set number of steps the motor is commanded to move the sample probe. In such cases, the imaging system further includes program instructions for recording the position of the sample probe when a change in capacitance equal to or greater than a predetermined threshold is detected or when the motor does not move the preset number of steps.

It is noted that FIG. 3 may be taken to illustrate a scenario when both the step loss detection method and the capacitance monitoring method are used for calibrating the sample probe position or may be taken to illustrate scenarios which include either the step loss detection method or the capacitance monitoring method. In any case, the process depicted in FIG. 3 may continue to block 88 after either or both of the step loss detection method and the capacitance monitoring method are conducted. At block 88, a determination is made as to whether step loss is detected or an electrically conductive material is detected. In cases in which detection is made, the process continues to block 89 to calibrate the position of the sample probe. In particular, the processes associated with block 89 may include program instructions for recording the current position of the sample probe as a reference position when a change in capacitance equal to or greater than a predetermined threshold is detected (e.g., when a change in voltage associated with the capacitance between the sample probe and the storage vessel platform is detected to be equal to or greater than a predetermined threshold) or when the motor does not move the preset number of steps. In addition, the processes associated with block 89 may include program instructions for designating a target vertical position of the sample probe for extracting fluid assays from wells of the storage vessel based on the reference position.

In general, the distance between the designated target vertical position of the sample probe relative to the reference position of the sample probe may be selected depending on the specifications of the system, and, thus, may vary among systems. A general objective of the designated target vertical position, however, is for the sample probe to be able to aspirate a sample contained in the well and, therefore, the designated target vertical position may preferably be arranged in the lowermost half of the well spaced above the bottom surface of the well. In some cases, the target vertical position may be designated at a position a set distance from the reference position farther from the storage vessel platform. Such a scenario may be particularly applicable when the reference position of the sample probe is at the bottom of a well (i.e., when no electrically conductive material is placed in the well and the step loss method is used to determine the reference position of the sample probe). In particular, in order to effectively aspirate a sample from a well of a storage vessel, it is generally beneficial for the sample probe to be spaced apart from the bottom surface of the well such that the opening of the sample probe is not blocked.

In other embodiments, the reference position of the sample probe may be designated as the target vertical position of the sample probe. Such a scenario may be particularly applicable when the reference position of the sample probe is spaced apart from the bottom of a well (i.e., when an electrically conductive material is placed in the well and either the capacitance monitoring method or the step loss method is used to determine the reference position of the sample probe). In particular, when an electrically conductive material is placed in a well, detection of the electrically conductive material may generally set a reference position of the sample probe above a bottom surface of the well and, in some cases, the reference position may be suitable for aspirating a sample from the well. In other cases, however, the target vertical position may be designated at a distance apart from a reference position which has been recorded based upon detection of an electrically conductive material within the well. In such cases, the target vertical position may be designated farther away or closer to the bottom surface of the well relative to the recorded reference position. In particular, if an electrically conductive material causes a reference position to be recorded which is in the upper portion of the well, it may be advantageous to designate the target vertical position deeper within the well, but above the bottom surface of the well. Conversely, when reference position is recorded very close to the bottom surface of the well, it may, in some embodiments, be advantageous to designate the target vertical position farther away from a bottom surface of the well.

In cases in which both capacitance and step loss are monitored to determine a reference position of the sample probe within a well, the imaging system described herein may be configured to selectively designate the target vertical position different distances from the reference position based upon which of the two methods is detected to set the reference position of the sample probe. More specifically, the imaging system may, in some embodiments, include program instructions for selectively designating the target vertical position different distances from the reference position based upon whether a change in capacitance equal to or greater than a predetermined threshold is detected (which may be alternatively stated as whether a change in an output signal related to capacitance, such as voltage, equal to or greater than a predetermined threshold is detected) or whether the motor not moving the set number of steps is detected. In particular, as set forth above, it may be advantageous to designate the target vertical position different distances from the recorded reference position depending the method used to determine the reference position and, thus, it may be advantageous to impart such selectivity into program instructions for the imaging system.

A further embodiment for the imaging system described herein is to include program instructions for removing the drive current applied to the motor upon detecting the motor does not move the set number of steps (i.e., via step loss detection) and pausing a set amount of time subsequent to removing the drive current and prior to recording the reference position. Such an embodiment may be advantageous for systems in which the storage vessel platform is prone to bending from force of the sample probe when the sample probe contacts either the bottom surface of the well or a solid object arranged in the well. In particular, a storage vessel platform may be prone to bend from such a force, distorting the depth to which the sample probe may be moved and, thus, distorting the reference position of the sample probe. In order to avoid such an inaccuracy, the imaging system described herein may be configured to interrupt the drive current applied to the motor moving the sample probe and, thus, remove the force applied to the storage vessel platform to allow the storage vessel platform to deflect back to its regular position. After allowing a particular amount of time for the deflection, a more accurate reference position of the sample probe may be recorded.

Referring again to FIG. 3, in cases in which neither step loss nor a change in capacitance above a predetermined threshold (or a change voltage greater than a predetermined threshold) is detected at block 88, the calibration routine routes back to block 72 to command the motor to move the probe another set number of motor steps. The number of motor steps may be the same or different from the previous passing of block 72. Thereafter, the routine repeats the monitoring of capacitance and/or the number of steps the motor moves as outlined in blocks 80-86 and 74-78, respectively. In general, the processes outlined in blocks 72, 74-78, and/or 80-86 are repeated until a target vertical position is designated or a predetermined number of iterations of the processes is conducted.

A further objective of the imaging system described herein is to introduce and immobilize a substantially uniform distribution of particles within the fluidic flow-through chamber of the system. Such an objective may be achieved in a number of manners, including configurations of an immobilization system having a magnet and a mechanism for selectively positioning the magnet in proximity to an imaging region of the fluidic flow-through chamber. In addition, the fluidic flow-through chamber may be dimensionally and geometrically configured to provide a substantially uniform velocity distribution of fluid introduced into the chamber. Moreover, an interior back portion of the imaging region of the fluidic flow-through chamber may include a roughened surface to aid in immobilizing the particles within the imaging region. The specifics regarding each of these configurations are set forth in more detail below. It is noted that the imaging systems described herein may include any one or combination of such configurations and, therefore, the imaging systems described herein are not limited to a compilation of all of the configurations together.

Figure 4:
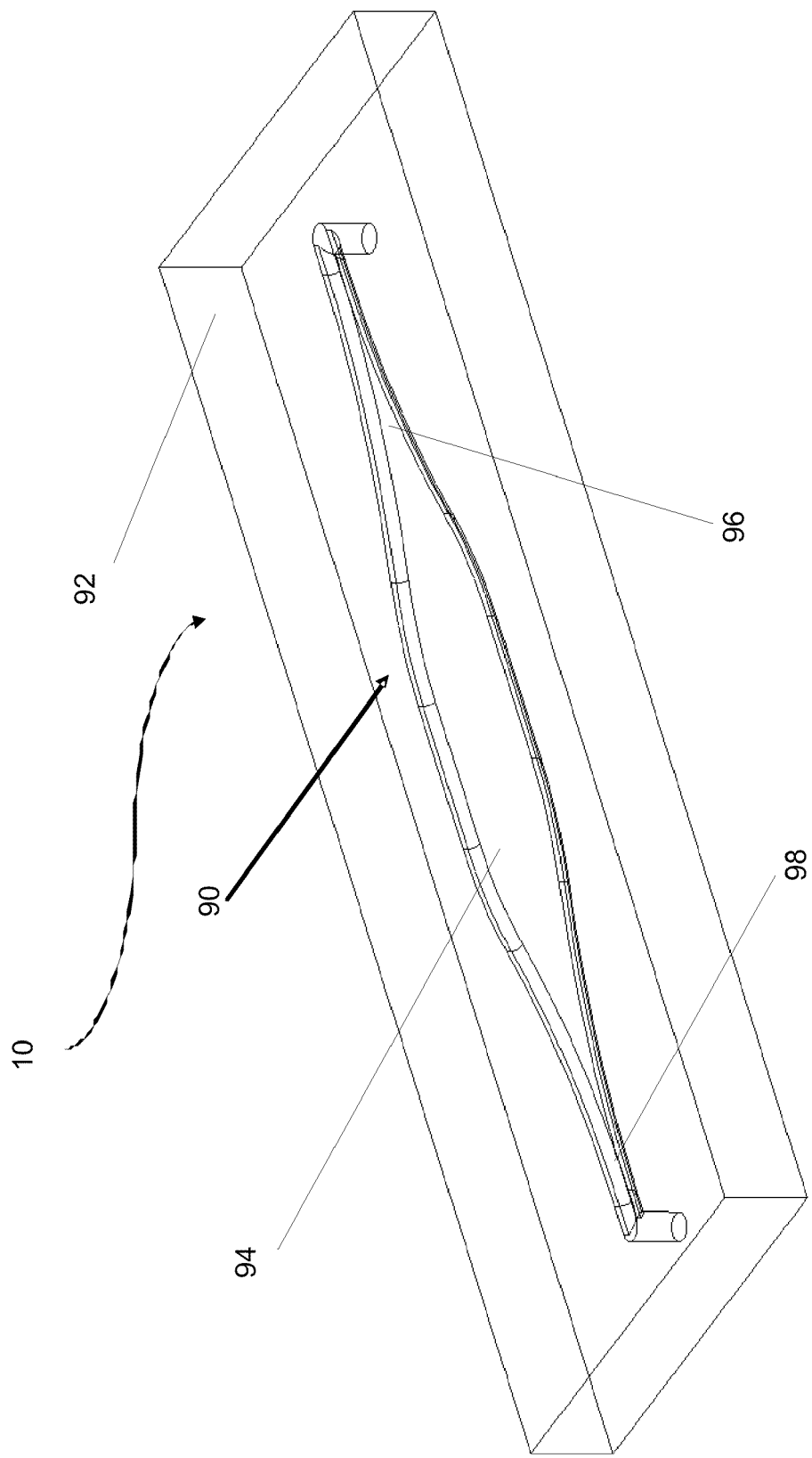
FIG. 4 illustrates a cross-sectional view of a fluidic flow-through chamber of an imaging system.

An exemplary configuration of fluidic flow-through chamber 10 is shown in FIG. 4 denoting an exemplary design for providing a substantially uniform velocity distribution of fluid introduced into the chamber. In addition, FIG. 4 illustrates an interior back portion of the imaging region of fluidic flow-through chamber 10 with a roughened surface for aiding the immobilization of particles. In general, fluidic flow-through chamber 10 includes micro-fluidic flow-through channel 90 disposed within support structure 92. Support structure 92 may include any material and configuration suitable for supporting channel 90 and allowing particles immobilized therein to be imaged. In particular, support structure 92 may generally include a support base for supporting channel 90 and further provide an optically clear path to imaging region 94 of channel 90. In some cases, channel 90 may not be covered (i.e., support structure 92 may merely include a support base to support channel 90). In other embodiments, however, it may be advantageous for channel 90 to be enclosed to prevent contamination of imaging region 94 and/or prevent the fluid introduced into fluidic flow-through chamber 10 from spilling out of the chamber. Thus, support structure 92 may, in some cases, include a cover as well as a support base in which the channel resides. In specific embodiments, support structure 92 may include upper and lower slides fused together which respectively correspond to a cover and a support base. Such a configuration may be advantageous with regard to manufacturing fluidic flow-through chamber 10 in that channel 90 may be formed within the support base and later sealed by the fusion of a cover to the support base, offering a secure and stable fluid-flow structure for chamber 10.

In any case, support structure 92 may be composed of a single type of material or multiple materials. In some embodiments, the cover and/or support base of support structure 92 may include an optically clear material (such as but not limited to optically clear glass), particularly in the vicinity of imaging region 94 of channel 90 such that an illumination beam may be allowed to pass through the cover or support base to image particles immobilized in the channel. In some cases, a back portion of support structure 92 corresponding to at least imaging region 94 may be configured to provide negligible reflectance and transmittance with respect to wavelengths of light emitted by the illumination subsystem of optic subsystem 8. For example, a back portion of support structure 92 corresponding to at least imaging region 94 may be coated with a coating configured to provide negligible reflectance and transmittance with respect to wavelengths of light emitted by the illumination subsystem of optic subsystem 8. In other embodiments, a back portion of support structure 92 corresponding to at least imaging region 94 may include a structural material configured to provide negligible reflectance and transmittance with respect to wavelengths of light emitted by the illumination subsystem of optic subsystem 8. The term "structural material" as used herein may generally refer to a material constituting a bulk construction of the structure or portion of the structure at hand. The phrase "back portion of support structure 92" as used herein may generally refer to the side of support structure 92 opposite to which an illumination beam is imposed on imaging region 94 for imaging particles immobilized therein.

The configuration of a coating or a structural material to provide negligible reflectance and transmittance with respect to wavelengths of light emitted by the illumination subsystem of optic subsystem 8 significantly and advantageously reduces background noise during the image acquisitions. In particular, without such a coating or structural material, the light which passes by particles immobilized within imaging region 94 during an imaging process may be reflected back along with the light which is reflected off the particles, distorting the light collected by optic subsystem 8 for analyzing the particles. As described in more detail below in reference to FIG. 8, optic subsystem 8 includes an illumination subsystem configured to illuminate imaging region 94 of chamber 10 at an acute angle relative to plane of the imaging region. In addition, optic subsystem 8 includes a photosensitive detection subsystem configured to image imaging region 94 when illuminated. The photosensitive detection subsystem is configured to collect light reflected from particles immobilized in the imaging region and thus, is arranged on the same side of fluidic flow-through chamber 10 as the illumination subsystem. As set forth in more detail below, immobilization subsystem 9 is generally configured to selectively move a magnet in the vicinity of the other side of fluidic flow-through chamber 10 such that particles may be immobilized within imaging region 94. This "other side" of fludic flow-through chamber 10 is referred to herein as the back portion of fluidic flow-through chamber 10 and corresponds to the back portion of support structure 92. If such a back portion of support structure 92 is optically transparent or translucent, light passing by particles immobilized within imaging region 94 during an imaging process may pass to the magnet of immobilization subsystem 9 and reflect back to the detectors of the photosensitive detection system, causing background noise for analyzing the particles. However, inclusion of a coating or a structural material as described above for the back portion of support structure 92 will, for the most part, absorb the light and, thus, such background noise will be significantly reduced.

In general, the configuration of a coating or a structural material to provide negligible reflectance and transmittance depends on the wavelengths of light to be emitted by optic subsystem 8 and, thus, options for coatings and structural materials may vary among systems. Dark coatings and structural materials may be suitable for a number of wavelengths of light and, thus, may be good options for the back portion of support structure 92. Exemplary coatings include but are not limited to black chrome oxide, black paint, and black epoxy. Exemplary structural materials include but are not limited to black epoxy and black quartz. The coating or structural material may be disposed on the interior or the exterior portion of support structure 92 and, in some cases, the coating and/or structural material may comprise both surfaces. In some cases, disposing the coating or structural material on the interior of support structure 92 may advantageously aid in providing a particular roughness to imaging region 94 to facilitate a distribution of particles which is suitable for imaging as described in more detail below. However, coatings disposed on the interior of a support structure may be particularly susceptible to erosion due to the exposure of moving fluids and particles. To avoid having to recoat and/or replace a support structure, it may be advantageous to additionally or alternatively employ a coating on the exterior surface of the support structure and/or employ a structural material for the back portion of the support structure.

In some cases, employing a coating on the back portion of a support structure to provide negligible reflectance and transmittance with respect to wavelengths of light emitted by an illumination subsystem may be advantageous for support structures having an optically transparent and/or translucent back portion. For example, in configurations described above in which upper and lower slides are fused together to make support structure 92 and particularly when such slides are made of the same optically clear material, it may be advantageous to coat an interior or exterior surface of a back portion of the support structure (i.e., prior to or after fusing the slides together). In addition or alternatively, employing a coating on a back portion of a support structure may be advantageous for retrofitting support structures having an optically transparent and/or translucent back portion. In other cases, it may be advantageous to employ a structural material on the back portion of a support structure to provide negligible reflectance and transmittance with respect to wavelengths of light emitted by an illumination subsystem since structural materials may be less susceptible to erosion and, thus, less maintenance may be needed with such an option.

As noted above, an interior back portion of imaging region 94 may include a roughened surface which aids in immobilizing particles within the imaging region. The phrase "interior back portion of imaging region 94" as used herein may generally refer to a portion of imaging region 94 interior to channel 90 upon which particles are immobilized. As set forth below, such an interior back portion corresponds to a back side of imaging region 94, which refers to the side of imaging region 94 adjacent to magnet 100 when the magnet is brought in proximity to fluidic flow-through chamber 10. Alternatively stated, the back side of imaging region 94 is opposite to the side of fluidic flow-through chamber 10 where an illumination beam is imposed on imaging region 94 for imaging particles immobilized therein, which may be referred to herein as the "front side of imaging region 94". It is noted that the system described herein may be configured such that the immobilization system is positioned on underside of fluidic flow-through chamber 10 (e.g., see, FIG. 8) and, thus, the "back portion of the imaging region 94" may be referred to as a "floor" of the imaging region in some embodiments. The system described herein, however, is not necessarily so limited and may alternatively have an immobilization system positioned on a top side of fluidic flow-through chamber 10 (and the optic subsystem positioned on an underside of the chamber). In yet other embodiments, fluidic flow-through chamber 10 may be positioned sideways (e.g., see, FIG. 1).

Optimally, the surface roughness along the back portion of imaging region 94 is sufficient to prevent particles from sliding along the back portion of imaging region 94 as particles are brought into contact with the imaging region floor by the magnet of the immobilization system. Without such surface roughness, particles may be prone to slide along the back portion of the imaging region, causing the particles to cluster at the down-end stream area of the imaging region. In general, particle clustering is undesirable since the proximity of the particles may induce measurable reflections and, further, light collected from a cluster is generally difficult to differentiate on a particle by particle basis. It is noted that while the surface roughness employed may be sufficient to prevent particles from sliding along the back portion of imaging region 94, the surface roughness should not affect the level of the imaging region floor to ensure all immobilized particles fall on the same imaging plane. An exemplary range of surface roughness for the back portion of imaging region 94 which has shown to be suitable for preventing particles from sliding is between approximately 0.4 microns root mean square and approximately 1.0 micron root mean square and, more preferably between approximately 0.6 microns root mean square and approximately 0.8 microns root mean square. Smaller and larger magnitudes of surface roughness, however, may be employed, depending on a number of matters, including but not limited to fluid flow rate, particle size, and strength of the magnet employed in the immobilization system.

The surface roughness may be facilitated in a number of manners, including fabricating channel 90 in a manner which generates a particular surface roughness, such as etching (e.g., microblasting) channel 90 or, more specifically, imaging region 94 within support structure 92. Alternatively, channel 90 or, more specifically, imaging region 94 may be fabricated from a material having a surface roughness sufficient to prevent particles from sliding along the back portion of imaging region 94. In yet other embodiments, channel 90 or, more specifically, imaging region 94 may be coated with a coating having elements sufficient to impart a surface roughness which prevents particles from sliding along the back portion of imaging region 94. As noted above, in some embodiments, the material used to impart surface roughness on the floor of imaging region 94 may further serve to provide negligible reflectance and transmittance with respect to wavelengths of light emitted by the illumination subsystem of optic subsystem 8. In any case, it is noted that in embodiments in which channel 90 is enclosed (i.e., when support structure 92 includes a cover), both the interior and exterior surfaces of the front side of imaging region 94 include substantially smooth surfaces (e.g., having surface roughnesses of approximately 0.025 microns root mean square or less). The smooth surfaces are generally advantageous such that images with little or no distortion may be obtained.

As shown in FIG. 4, channel 90 may include inlet channel 96 and outlet channel 98 for respectively introducing and discharging a fluid assay into and out of imaging region 94. In addition, channel 90 may include inlet and outlet ports respectively coupled to channels 96 and 98 for receiving and dispensing a fluid assay to and from fluidic flow-through chamber 10. Although the inlet and outlet ports are shown in the lower side of support structure 92, fluidic flow-through chamber 10 is not necessarily so limited. As noted above, fluidic flow-through chamber 10 and, more specifically, channel 90 may be dimensionally and geometrically configured to provide a substantially uniform velocity distribution of fluid introduced into the chamber. In particular, as shown in FIG. 4, the widths of channel input channel 96 and output channel 98 may be tapered relative to a width of imaging region 94. Such tapering may generally aid in creating a uniform velocity distribution of a fluid assay introduced through channel 90. In particular, a fluid assay introduced into channel 90 may gradually disperse as it flows through the channel, creating a substantially uniform velocity distribution of the fluid, which in turn may generally distribute the particles in a more uniform manner, particularly in imaging region 94. In some cases, channel 90 may have rounded edges to further facilitate a uniform velocity distribution of a fluid assay within channel 90. In particular, rounded edges may reduce or eliminate the possibility of eddy currents within channel 90, which may undesirably disrupt fluid flow within channel 90.

In general, the dimensions of channel 90 may vary depending on the design specifications and operating conditions of a system. Exemplary widths of channels 96 and 98 at the inlet and outlet ports, respectively, may be approximately 0.5 mm and may gradually increase/decrease to/from approximately 4 mm at imaging region 94. The width of imaging region 94 in general may not vary. Smaller or larger widths may be considered for the inlet/outlet ports, channels 96 and 98, and imaging region 94. The depth of channel 90 may vary among systems as well, but may generally be greater than the widths of the particles to be imaged and, in some cases if the sample probe used to aspirate a sample includes a filter, the depth of the channel may be greater than the widths of the filter pores. In order to help facilitate a uniform velocity distribution within channel 90, it may be advantageous to limit the depth of the channel, such as but not limited to less than approximately 800 microns. An exemplary depth range of channel 90 which may be particularly suitable for the imaging system described herein may be between approximately 200 microns and approximately 600 microns, but smaller and larger depths may be considered. The configuration of the channel geometry to create a uniform velocity distribution is dependent on the volumetric flow rate of the fluid in channel 90 and may generally range between 8 μl/sec and 12 μl/sec for particle introduction into the channel, and can be increased up to about 250 μl/sec for chamber cleaning Smaller or larger fluidic flow rates, however, may be used.

There are two primary modes of operating fluid handling subsystem 6 to load a sample in fluidic flow-through chamber 10, namely a load procedure with sample wash and a load procedure without sample wash. Referring to FIG. 1, the load procedure with no sample wash generally occurs as follows:

Clean System
1) Position pump valve 20 to pump from container 22.
2) Load Drive Solution.
3) Position pump valve 20 to pump to sample loop 16.
4) Position sample valve 18 to pump to chamber 10.
5) Move magnet away from chamber 10).
6) Pump drive solution through chamber to clean chamber 10.
7) Position sample valve 18 to pump to probe 15.
8) Pump drive solution through probe 15 to clean probe.

Load Sample
1) Position pump valve 20 to pump from container 22.
2) Load Drive Solution.
3) Position pump valve 20 to pump to sample loop 16.
4) Position sample valve 18 to pump from probe 15.
5) Lower probe 15 into sample well 12.
6) Load a sample into sample loop 16.
7) Raise probe 15 and pull until air is at sample valve 18 and entire sample is in sample loop 16.
8) Position sample valve 18 to pump to chamber 10.
9) Move magnet toward chamber 10.
10) Pump sample from sample loop 16 into chamber 10 capturing magnetic beads.
11) Take Images with the sample immobilized.

Clean System
1) Position pump valve 20 to pump from container 22.
2) Load Drive Solution.
3) Position pump valve 20 to pump to sample loop 16.
4) Position sample valve 18 to pump to chamber 10.
5) Move magnet away from chamber 10.
6) Pump drive solution through chamber 10 to clean chamber.
7) Position sample valve 18 to pump to probe 15.
8) Pump drive solution through probe 15 to clean probe.

The load procedure with sample wash generally occurs as follows:

Clean System
1) Position pump valve 20 to pump from container 22.
2) Load Drive Solution.
3) Position pump valve 20 to pump to sample loop 16.
4) Position sample valve to pump to chamber 10.
5) Move magnet away from chamber 10.
6) Pump drive solution through chamber 10 to clean chamber.
7) Position sample Valve 18 to pump to probe 15.
8) Pump drive solution through probe 15 to clean probe.

Preload Wash Solution
1) Position pump valve 20 to pump from container 22.
2) Load Wash Solution.
3) Pump Valve 20 to pump to sample loop 16.
4) Position sample valve to pump to chamber 10.
5) Pump wash solution through chamber.
6) Position sample valve 18 to pump to probe 15.
7) Pump wash solution through probe 15 (sample loop 16 and probe 15 preloaded with Wash Solution).

Load Sample
1) Position pump valve 20 to pump from container 22.
2) Load Drive Solution.
3) Position pump valve 20 to pump to sample loop 16.
4) Position sample valve 18 to pump from probe 15.
5) Lower probe 15 into well 12.
6) Load Sample into sample loop 16.
7) Raise probe 15 and pull until air is at sample valve and entire sample is in sample loop 16.
8) Position sample valve 18 to pump to chamber 10.
9) Move magnet toward chamber 10.
10) Pump sample from sample loop 16 into chamber 10 capturing magnetic beads.
11) Pump wash solution in sample loop 16 behind sample over captured magnetic beads to "Wash" beads.
12) Take Images with the sample immobilized.

Clean System
1) Position pump Valve 20 to pump from container 22.
2) Load Drive Solution.
3) Position pump valve 20 to pump to sample loop 16.
4) Position sample valve 18 to pump to chamber 10.
5) Move magnet away from chamber 10.
6) Pump drive solution through chamber 10 to clean chamber.
7) Position sample Valve 18 to pump t probe 15.
8) Pump drive solution through probe 15 to clean probe.

Unlike a flow cytometer, the system of the present invention provides the ability to dispense with the fluid surrounding the beads, thereby washing away the free fluorochromes. This is possible because the beads are magnetically attached to the substrate (when the magnet is brought into contact with the back of the chamber), and will remain so if a new "fresh" fluid plug is injected into the chamber, thereby displacing the fluorochrome laden liquid. For the convenience of processing, some assays do not perform this final wash step, resulting in excitation of the extraneous fluorophores, and increased "background" signal when the assay response from beads is measured. However, these no-wash assays have a poorer limit of detection than washed assays. Thus, it may be found to be advantageous in some instances to use the second loading procedure detailed above where the sample is "washed" to remove from the surrounding solution fluorochromes that are not bound to the surface of a bead.

Figure 5:
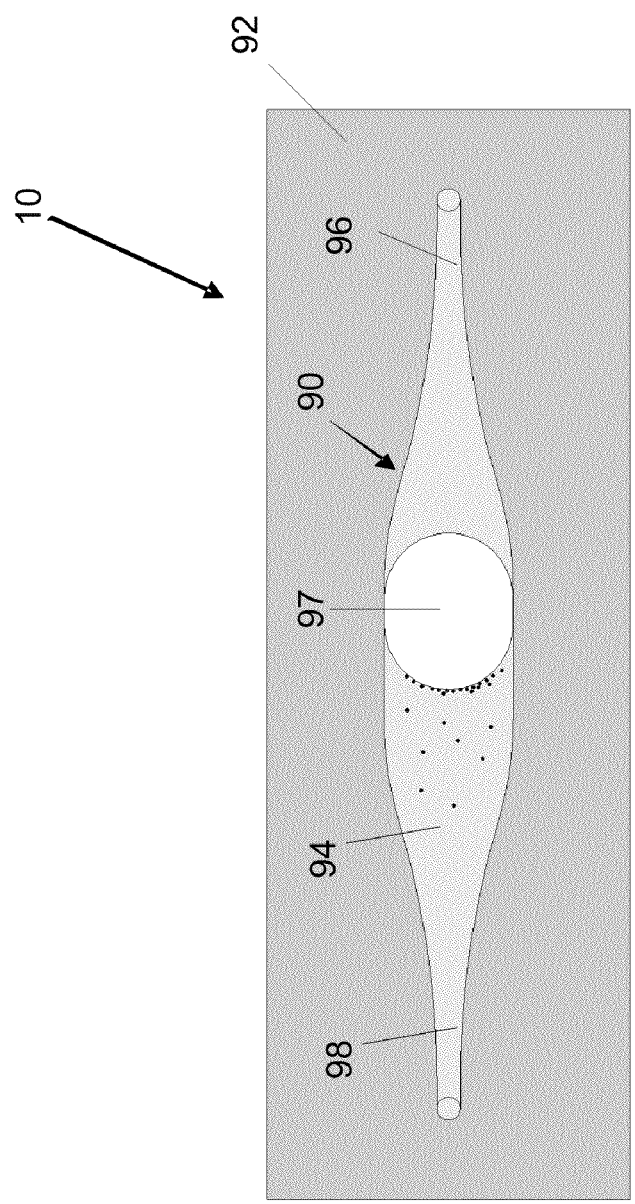
FIG. 5 illustrates the fluidic flow-through chamber depicted in FIG. 4 with a gas bubble moving between the inlet and outlet of the chamber.

Once the magnetic particles are captured and imaged, the next step is to remove them from the chamber so that a new set of magnetic particles can flow in, be captured and imaged. In some embodiments, particles may be removed from fluidic flow-through chamber 10 by disengaging a magnetic field used to immobilize the particles within imaging region 94 (e.g., by moving a magnet away from the imaging region) such that immobilized particles are released from the surface of the imaging region. Thereafter or during such a release process, a gas bubble may be flowed through the chamber such that the released particles are removed from the chamber. An intermediary stage of such a process is shown in FIG. 5. In particular, FIG. 5 illustrates air bubble 97 within imaging region 94 coming into contact with particles and pushing them along as the air bubble traverses channel 90 between the inlet/outlet ports coupled to channels 96 and 98.

In some cases, gas bubble 97 is of sufficient size to span the cross-sectional area of channel 90 while moving through the chamber. In this manner, the air bubble may be large enough to displace fluid on all sides of channel 90 so that it forms an air water interface spanning the entire surface area of the channel. In general, the air water interface has relatively high surface tension such that as gas bubble 97 travels through channel 90, it acts like a plunger sweeping the particles out of the channel as it passes through. Thus, in the load procedures described above, cleaning of the chamber after particles have been imaged may include flowing an air bubble through fluidic flow-through chamber 10 after step 5 in the Clean System routine after imaging has been performed and, optionally, after flowing drive solution through the chamber. In any case, gas bubble 97 may include any substantially inert gas, including but not limited to air or nitrogen.

As set forth above, an immobilization system for the imaging system described herein may include a magnet and a mechanism for selectively positioning the magnet in proximity to an imaging region of a fluidic flow-through chamber. Turning to FIG. 6, an exemplary configuration of immobilization subsystem 9 including such components is broadly illustrated. In particular, immobilization subsystem 9 is shown in FIG. 6 positioned on a side of fluidic flow-through chamber 10 which is opposite optics subsystem 8. It is noted that optics subsystem 8 is not shown in FIG. 6 to simplify the drawing, but the placement of optic subsystem 8 and immobilization subsystem 9 relative to fluidic flow-through chamber 10 is shown in FIG. 8. In addition, the depiction of fluidic flow-through chamber 10 in FIG. 6 is taken along the side view of channel 90 with inlet channel 96 on the bottom and outlet channel 98 on the top, denoting the direction of fluid flow.

As depicted in FIG. 6, immobilization subsystem 9 may include magnet 100 and mechanism 102 for selectively positioning magnet 100 in proximity to imaging region 94 of fluidic flow-through chamber 10. It is noted that although a single magnet is shown in FIG. 6, immobilization subsystem 9 may include more than one magnet, each positioned proximate the side of the fluidic flow-through chamber 10 opposite optics subsystem 8. In addition, although magnet 100 is shown as a cylindrical magnet, magnet 100 may be of a different a dimensional configuration. It is further noted that the configuration of mechanism 102 may vary relative to one illustrated in FIG. 6. In particular, alternative mechanisms for moving magnet 100 toward and away from fluidic flow-through chamber 10 may be considered, including those which move magnet 100 in a direction along a plane parallel to the adjacent surface of fluidic flow-through chamber 10, rather than along a plane perpendicular to such a surface as described in more detail below.

In general, magnet 100 may be a magnet known in the art, such as a permanent magnet (e.g., a Neodynium N42 cylindrical magnet polarized along its cylindrical axis), and may be configured to generate a magnetic field suitable for attracting and substantially immobilizing magnetically responsive particles along a surface of imaging region 94 of fluidic flow-through chamber 10. For example, magnet 100 may generally have cross-sectional dimensions (as taken along a plane parallel to the imaging surface of imaging region 94) which are equal, similar or smaller than the imaging plane of imaging region 94 such that particles may be prevented from being immobilized within channels 96 and 98. In addition, the strength of the magnetic field generated by magnet 100 may vary, depending on the design characteristics of the imaging system, but may generally be strong enough to pull the magnetically responsive particles toward an imaging surface of imaging region 94 without causing particles to cluster. In particular, the strength of magnet 100 is preferably selected such that particles are attracted to the surface of imaging region 94 adjacent to magnet 100 and immobilized in a distributed manner.

As described above in reference to FIG. 4, due to the configurations of channel 90 of fluidic flow-through chamber 10 to induce a substantially uniform velocity distribution of fluid therethrough, particles suspended in an aqueous solution introduced into the chamber may be evenly distributed throughout the channel as they approach imaging region 94. As the magnetically responsive particles flow through a magnetic field produced by magnet 100, they are drawn down to the imaging surface of imaging region 94 towards the magnet and held in place. As further described in more detail above in reference to FIG. 4, the immobilization of the particles may, in some embodiments, involve a combination of the applied magnetic field and a roughened surface of the imaging region.

Mechanism 102 may generally include any configuration for selectively moving magnet 100 toward and away from imaging region 94 of fluidic flow-through chamber 10. More specifically, mechanism 102 may include any configuration for moving magnet 100 between an active position (i.e., a position in proximity to imaging region 94 sufficient to attract and substantially immobilize magnetically responsive particles against a surface of the imaging region based on the magnetic field generated by magnet 100) and an inactive position (i.e., a position far enough away from imaging region 94 to release the particles from the imaging surface based on the magnetic field generated by magnet 100). As shown in FIG. 6, mechanism 102 may include linear actuator 104 (e.g., a slide) to effect such movement of magnet 100, but other actuators known in the art for moving objects may be used.

In any case, mechanism 102 may, in some embodiments, be configured to prevent magnet 100 from contacting fluidic flow-through chamber 10 when the magnet is positioned in proximity to imaging region 94. For example, mechanism 102 may include hardstop 106 within fluidic line housing 109 to halt the movement of linear actuator 104 when magnet 100 is moved in the vicinity of fluidic flow-through chamber 10 as shown in FIG. 6. In alternative embodiments, mechanism 102 may include a hardstop spaced a small distance from fluidic flow-through chamber 10 along the path of magnet 100 such that movement of magnet 100 may be halted when it is moved in the vicinity of the chamber. The spacing of hardstop 106 relative to fluidic flow-through chamber 10 in such embodiments may vary among systems, but may generally be less than or equal to approximately 1.0 mm and preferably, between approximately 0.3 mm and approximately 0.7 mm. In any case, allowing magnet 100 to contact fluidic flow-through chamber 10 may cause damage to the chamber, particularly through repeated operations, and thus, incorporating a configuration within mechanism 102 to prevent such contact may be advantageous.

In some embodiments, mechanism 102 may be configured to position magnet 100 such that its polarizing axis is aligned with a central point of imaging region 94 when magnet 100 is positioned in proximity to the imaging region. In other cases, as set forth in more detail below and shown in FIG. 6, it may be advantageous for mechanism 102 to position magnet 100 such that its polarizing axis 108 is located downstream relative to a central point 110 of imaging region 94 when the magnet is positioned in proximity to the imaging region. In such embodiments, since magnet 100 may generally have cross-sectional dimensions which are equal, similar or smaller than the imaging plane of imaging region 94, mechanism 102 may be additionally configured such that a leading edge 112 of the magnet is located downstream relative to a leading edge 114 of imaging region 94 when the magnet is positioned in proximity to the imaging region. In general, the term "leading edge" as used herein may refer to the foremost edge of a component or region relative to another component or region in a system, particularly with respect to a direction of fluid flow within the system. For instance, reference to the leading edges of magnet 100 and imaging region 94 as used herein may refer to the foremost edges of magnet 100 and imaging region 94 relative to inlet channel 96 of channel 90 of fluidic flow-through chamber 10. In any case, the specific offset spatial location of magnet 100 relative to the central point of imaging region 94 may vary among systems, depending on the design characteristics and operating parameters of the systems (e.g., the size of the magnet and the flow rate at which fluid is pumped through the fluidic flow-through chamber).

Contrary to what might be expected, co-alignment of the polarizing axis 108 of the magnet 100 and a central point 110 of imaging region 94 does not produce optimal distribution of particles within imaging region 94 because the magnetic field lines extend across a larger surface area than the magnet itself. As a result, particles flowing through the chamber begin to be influenced by the magnetic field of the magnet before reaching imaging region 94. However, it was discovered during the development of the system described herein that offsetting the polarizing axis of the magnet downstream relative to a central point of the imaging region and spacing the leading edge of the magnet downstream of the leading edge of the imaging region may advantageously combat such a problem and aid in facilitating a larger number of immobilized particles within the imaging region.

Figure 7:
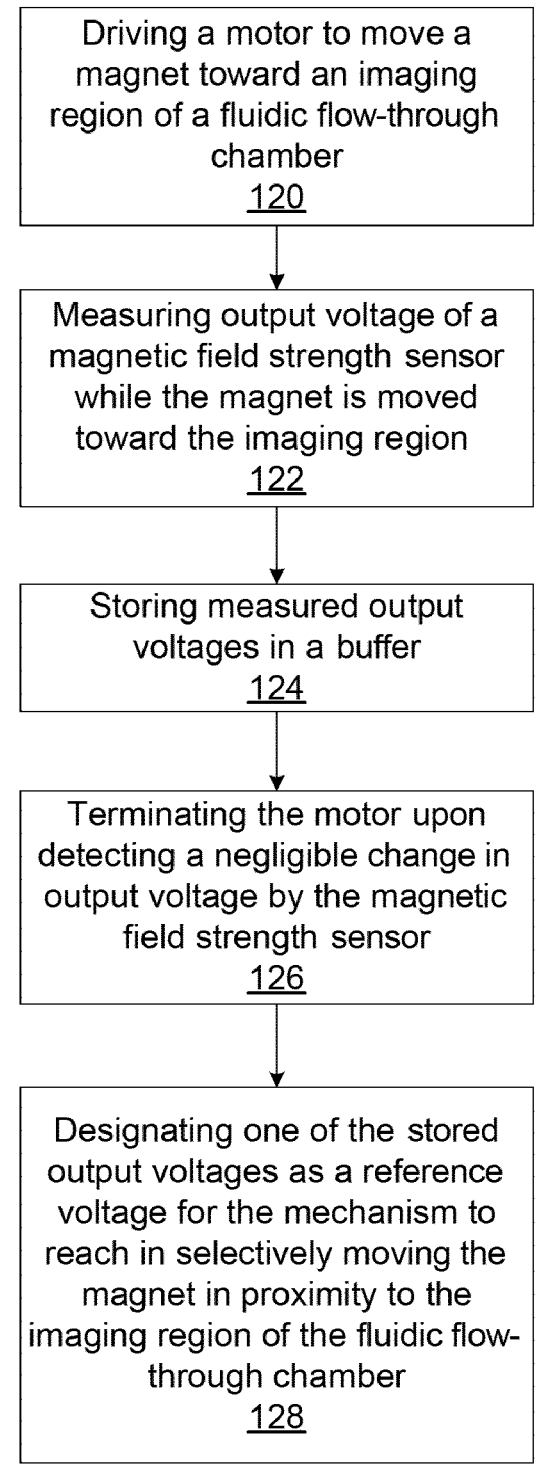
FIG. 7 is a flowchart of a method for calibrating a position to which a mechanism of the immobilization system depicted in FIG. 6 is to move a magnet in proximity to a fluidic flow-through chamber.

In some embodiments, the location to which magnet 100 is moved in the vicinity of fluidic flow-through chamber 10 may be predetermined (i.e., the spacing between magnet 100 and fluidic flow-through chamber when magnet 100 is brought in to the vicinity of the chamber may be predetermined) and, in some cases, set by a calibration routine. An exemplary calibration routine is shown in FIG. 7. As set forth in more detail below, in order to affect such a routine, mechanism 102 may include a magnetic field strength sensor 105, such as a Hall effect sensor, mounted near fluidic flow-through chamber 10. In addition, the system may include program instructions executable by a processor for performing the routine, specifically for calibrating a position of magnet 100 to which mechanism 102 is used to selectively move the magnet in proximity to imaging region 94 of fluidic flow-through chamber 10. As shown in blocks 120, 122 and 124 of FIG. 7, the calibration routine may include driving a motor to move a magnet toward an imaging region of a fluidic flow-through chamber and while the magnet is moved toward the imaging region output voltage of a magnetic field strength sensor may be measured and stored in a buffer. The buffer may include any configuration known in the art, including but not limited to a circular buffer. In reference to FIG. 6 for such process steps, as the linear actuator 104 translates the magnet 100 towards fluidic flow-through chamber 10, the voltage output of magnetic field strength sensor 105 increases or decreases depending on the polarity of the magnet.

When the magnet reaches hard stop 106, the voltage output of magnetic field strength sensor 105 becomes constant. As such, the calibration routine includes terminating the motor upon detecting a negligible change in output voltage by the magnetic field strength sensor as shown in block 126 of FIG. 7. At such a point, one of the stored output voltages may be designated as a reference voltage for mechanism 102 to reach in selectively moving the magnet in proximity to imaging region 94 of fluidic flow-through chamber 10 as denoted in block 129. In general, any of the stored output voltages may be designated as a reference voltage, but it may be particularly advantageous to designate a voltage different than the voltage associated with the negligible change in voltage detected at block 126 (i.e., designate a voltage measured prior to the magnet reaching hard stop 106). In particular, it may be advantageous to calibrate the location to which magnet 100 is moved in the vicinity of fluidic flow-through chamber 10 to be spaced apart from hard stop 106 such that magnet 100 or mechanism 102 is not repeatedly brought into contact with hard stop 106 during the operation of the system. In particular, allowing magnet 100 or mechanism 102 to repeatedly contact hard stop 106 may cause damage to the magnet, mechanism and/or hard stop.

An alternative method for calibrating the location to which magnet 100 is moved in the vicinity of fluidic flow-through chamber 10 is to drive the magnet a predetermined number of motor steps away from the imaging region of the fluidic flow-through chamber after a negligible change in voltage is detected in reference to block 126. More specifically, the motor may be driven a predetermined number of motor steps to move the magnet away from the imaging region of the chamber. As noted above, hard stop 106 is at a predetermined location relative to fluidic flow-through chamber 10 and, therefore, may be used as a reference location for calibrating the position of magnet 100. The predetermined number of motor steps may be any number of steps, including a single step or multiple steps, depending on the specifications of the system. Subsequent to moving the magnet the predetermined number of motor steps, the output voltage of the magnetic field strength sensor may be measured and the measured output voltage may be designated as a reference voltage for the mechanism to reach in selectively moving the magnet in proximity to the imaging region of the fluidic flow-through chamber. Such a routine does not rely on retrieving stored output voltages and, thus, in some embodiments, the process outlined in block 124 of FIG. 7 may be omitted from a calibration routine which includes driving the magnet back a predetermined number of motor steps.

Regardless of the calibration routine employed, the system described herein may include an automated routine (i.e., program instructions executable by a processor) for commanding mechanism 102 to stop movement of magnet 100 relative to a reference voltage associated with a position in proximity to imaging region 94 of fluidic flow-through chamber 10 (e.g., the reference voltage designated by either of the calibration routines described above). In some cases, an automated routine for commanding mechanism 102 to stop movement of magnet 100 may include driving a motor of the mechanism to move the magnet toward imaging region 94 of fluidic flow-through chamber 10, monitoring output voltage of the magnetic field strength sensor while the magnet is moving, and terminating the motor upon detecting the reference voltage.

In other embodiments, an automated routine for commanding mechanism 102 to stop movement of magnet 100 may include driving a motor of the mechanism a predetermined number of steps to move the magnet toward the imaging region of the fluidic flow-through chamber and measuring output voltage of the magnetic field strength sensor after the motor has moved the predetermined number of steps. Upon detecting a difference between the measured output voltage and the reference voltage that is less than a predetermined threshold, the motor driving mechanism 102 may be terminated. Conversely, upon detecting a difference between the measured output voltage and the reference voltage which is greater than the predetermined threshold, corrective action may be affected. The corrective action may include a variety of actions, including but not limited to terminating the sample run or iteratively driving the motor a preset number of steps until a difference between a measured output voltage and the reference voltage is less than the predetermined threshold. In any case, the predetermined threshold may generally be based on the specifications of the system and the desired precision for moving the magnet to the designated reference position, and, thus, may vary among systems.

After signal acquisition by the measurement device, the magnetic field may be removed (by moving the magnet to the inactive position), and the particles may be removed from fluidic flow-through chamber 10 using the chamber cleaning routines described above and the introduction of an air bubble as described in reference to FIG. 5, followed by the introduction of new particles from the next sample into the chamber. The particles in fluidic flow-through chamber 10 may be removed and particles may be introduced to the chamber using any of the embodiments described herein.

Broadly speaking, the method of operating the imaging system described in reference to FIGS. 1-14 herein involves exposing the analytes of interest to a bead population to create a sample, which is stored in a sample storage vessel 12 as shown in FIG. 1. The sample is loaded into fluidic flow-through chamber 10, using, e.g. the sample handling steps described above. The sample is immobilized in fluidic flow-through chamber 10 by the selective operation of mechanism 102. Optionally, the immobilized sample can be washed to remove extraneous fluorophores. With the sample immobilized in chamber 10, an illumination module is operated to excite the sample. A photosensitive detector captures the image and the image is processed (see, e.g. U.S. Patent Application Ser. No. 60/719,010 entitled "Methods and Systems for Image Data Processing" filed Sep. 21, 2005 by Roth, which is incorporated by reference as if fully set forth herein.) Following image acquisition, mechanism 102 releases the particles by moving magnet 100 away from chamber 10 and the chamber is cleaned.

As noted above, FIG. 8 illustrates an exemplary configuration of components for optic subsystem 8. The system depicted in FIG. 8 includes light sources 132 and 134 (and additional light sources as required) which are configured to emit light having different wavelengths or different wavelength bands (e.g., one of the light sources may be configured to emit red light and the other light source may be configured to emit green light). The light emitted by light sources 132 and 134 may include, for example, light in any part of the visible and invisible wavelength spectrums. Light sources 132 and 134 may include light emitting diodes (LEDs) or any other suitable light sources known in the art. Light sources 132 and 134 are arranged above the periphery of fluidic flow-through chamber 10. In addition, the light sources are arranged above the chamber such that each light source directs light to particles in fluidic flow-through chamber 10 from a different direction. Although the system shown in FIG. 8 includes two light sources, it is to be understood that the system may include any suitable number of light sources. In some embodiments, six light sources (132, 134 and four additional light sources (not shown)) may be positioned in a circumferential or hexagonal arrangement to direct light onto the imaging plane. In this manner, the light sources may be configured to provide an illumination "ring".

The system also includes filters 136 and 138. Filters 136 and 138 may be bandpass filters or any other suitable spectral filters known in the art. In this manner, the system may use light sources 132 and 134 and filters 136 and 138 to sequentially illuminate the particles with different wavelengths or different wavelength bands of light. For example, red light may be used to excite classification dyes that may be internal to the particles, and green light may be used to excite reporter molecules coupled to the surface of the particles. Since the classification illumination is dark during reporter measurements (i.e., in the above example, red light is not directed to the particles while green light is directed to the particles), the analyte measurement sensitivity of the system will not be reduced due to crosstalk from out of band light. Although the system shown in FIG. 8 includes two lenses associated with each light source, it is to be understood that the system may include any suitable number of lenses for each light source. For example, in some embodiments, the system may include three refractive lenses for each light source to collect as much light from the light sources as possible and near-collimate it before presentation to a filter. Though a single normal refractive lens can be used, two or more lenses may be advantageous to increase the collection angle and provide a more efficient illumination system.

As shown in FIG. 8, the system also includes imaging lens 140 positioned at the center (or approximately the center) of the illumination "ring." Imaging lens 140 may include any suitable refractive optical element known in the art. Imaging lens 140 is configured to image light scattered and/or fluoresced from the particles onto photosensitive detector 144 via one or more optical elements, which may include optical bandpass filters as discussed below. In some cases, imaging lens 140 may be fixedly attached to a housing and, in further embodiments, may be fixedly attached to a housing to which fluidic flow-though chamber 10 is fixedly attached. In the latter embodiment, the spacing between imaging lens 140 and fluidic flow-through chamber 10 may, thus, be fixed. In some cases, the system may include temperature sensor 142 arranged on the barrel of imaging lens 140 as shown in FIG. 8. Such a temperature sensor may be advantageous for regulating a focal position of the photodetection subsystem relative to the temperature of the imaging lens as described in more detail below in reference to FIG. 10.

As noted above, optics subsystem 8 may include photosensitive detector 144. Photosensitive detector 144 may be a CCD, CMOS, or Quantum Dot camera or any other suitable imaging device known in the art which is configured to generate images. Although the system shown in FIG. 8 includes a single photosensitive detector, it is to be understood that the system may include any suitable number of photosensitive detectors as well as any number of filters and lens to aid in the generation of images, which may be collectively referred to herein as a "photodetection subsystem". In an exemplary system, the photodetection subsystem may include substrate 146 arranged between the detector 144 and imaging lens 140. Substrate 146 may include detection filter/s 148 which may be bandpass filter/s or any other suitable spectral filter/s known in the art. In some cases, substrate 146 may include a device configured to alternate different filters into the optical path of light exiting imaging lens 140. For example, substrate 146 may include a filter wheel assembly 149 as shown in FIG. 8 and described in more detail below.

In particular, filter wheel assembly 149 may generally include a rotatable filter wheel affixed to a wheel mount and multiple detection filters aligning the circumference of the rotatable filter wheel. Each of the detection filters is configured to transmit light of a different wavelength or a different wavelength band. As such, the wavelength or wavelength band at which an image of particles is acquired by photosensitive detector 144 may vary depending on the position of the filter wheel assembly, which corresponds to the filter in the optical path of light exiting imaging lens 140. In this manner, a plurality of images of the particles may be formed sequentially by imaging the particles, altering the position of the filter wheel, and repeating the imaging and altering steps until images at each wavelength or waveband of interest have been acquired by photosensitive detector 144. The system shown in FIG. 8 may, therefore, be configured to generate a plurality or series of images representing the fluorescent emission of particles at several wavelengths of interest.

In some cases, the system may be configured to supply a plurality or series of digital images representing the fluorescence emission of the particles to a processor (i.e., a processing engine). The system may or may not include the processor. The processor may be configured to acquire (e.g., receive) image data from photosensitive detector 144. For example, the processor may be coupled to photosensitive detector 144 in any suitable manner known in the art (e.g., via transmission media or one or more electronic components such as analog-to-digital converters). Preferably, the processor is configured to process and analyze these images to determine one or more characteristics of particles such as a classification of the particles and information about a reaction taken place on the surface of the particles. The one or more characteristics may be output by the processor in any suitable format such as a data array with an entry for fluorescent magnitude for each particle for each wavelength. Specifically, the processor may be configured to perform one or more steps of a method for processing and analyzing the images. Examples of methods for processing and analyzing images generated by a system are illustrated in U.S. Patent Application Ser. No. 60/719,010 entitled "Methods and Systems for Image Data Processing" filed Sep. 21, 2005 by Roth, which is incorporated by reference as if fully set forth herein. The systems described herein may be further configured as described in this patent application. In addition, the methods described herein may include any step(s) of any of the method(s) described in this patent application.

The processor may be a processor such as those commonly included in a typical personal computer, mainframe computer system, workstation, etc. In general, the term "computer system" may be broadly defined to encompass any device having one or more processors, which executes instructions from a memory medium. The processor may be implemented using any other appropriate functional hardware. For example, the processor may include a digital signal processor (DSP) with a fixed program in firmware, a field programmable gate array (FPGA), or other programmable logic device (PLD) employing sequential logic "written" in a high level programming language such as very high speed integrated circuits (VHSIC) hardware description language (VHDL). In another example, program instructions (not shown) executable on the processor to perform one or more steps of the computer-implemented methods described in the above-referenced patent application may be coded in a high level language such as C#, with sections in C++ as appropriate, ActiveX controls, JavaBeans, Microsoft Foundation Classes ("MFC"), or other technologies or methodologies, as desired. The program instructions may be implemented in any of various ways, including procedure-based techniques, component-based techniques, and/or object-oriented techniques, among others. Program instructions implementing the processes, routines, a calibration techniques described herein may be transmitted over or stored on a carrier medium (not shown). The carrier medium may be a transmission medium such as a wire, cable, or wireless transmission link. The carrier medium may also be a storage medium such as a read-only memory, a random access memory, a magnetic or optical disk, or a magnetic tape.

Figure 9:
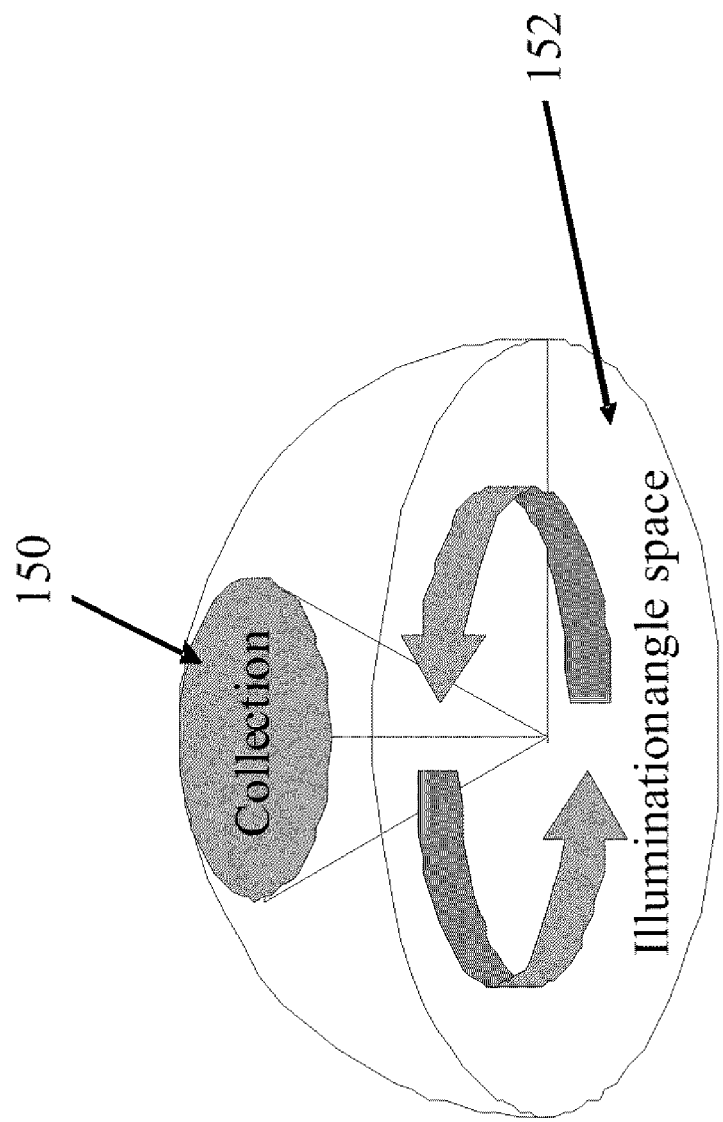
FIG. 9 is a schematic diagram of a collection and illumination angle space generated by an optics subsystem having a hexagonal arrangement of light sources.

In a preferred embodiment of the imaging system described herein, the position of photosensitive detector 144 in relation to light sources 132 and 134 as well as the positions of chamber 10 and immobilization subsystem 9 are optimized for imaging beads. Beads have distinct characteristics, namely the dye within the beads and reporter molecules on the beads that both absorb and re-emit photons in no preferred direction (uniformly over all angles). The preferred arrangement of light sources positioned evenly in a hexagonal arrangement with respect to imaging region 94 and photosensitive detector 144 is chosen to optimize the "angle space" of any beads in the Field of View (FOV) of the imaging sensors (any beads that can be seen by photosensitive detector 144). Since immobilization subsystem 9 is on the back of fluidic flow-through chamber 10, the angle space available for the illumination and photodetection subsystems is a hemisphere above the imaging region. This is illustrated in FIG. 9 where "collection" 150 is the solid angle collected by the photosensitive detector 144 and "illumination angle space" 152 is the space that the illumination modules (e.g., light sources 132, 134 and filters 136, 138) can occupy. The more coverage over this illumination angle space 152 by the illumination optics, the more illuminative power is imparted on the beads during imaging. Similarly, the higher the collection angle (Numerical Aperture) over the collection angle space 150, the more flux the imaging lens 140 can collect and deliver to the photosensitive detector 144. Thus, an optimal balance between the angles allocated for the photosensitive sensors and the illumination system can be achieved.

For low-cost manufacturability, the imaging lens 140 practical limit for numerical aperture is around 0.3 for a magnification of 4. For higher magnifications, the numerical aperture of imaging lens 140 could increase while maintaining the same cost guidelines. Other factors that affect the cost of the imaging lens 140 are Field of View and broadness of waveband. A numerical aperture of 0.3 is roughly 35 degrees full angle. The amount of excitation light delivered to the beads is limited in practice by the light source brightness and cost of excitation filters physically large enough to transmit all rays of light by the light source. The etendue of the light sources will dictate what of the bead's angle space is needed to provide the maximum flux over the field of view (FOV). (Etendue is the Area of the source multiplied by the solid angle of the source: it defines the geometry characteristics of the emitted flux.) If the FOV is relatively large, the angle space required will be lower and therefore more and/or brighter light sources can be used. However, more light sources will add cost to the system. Again, a balance between costs vs. performance must be determined. Conservation of brightness dictates that the etendue must be preserved in an optical system to maximize efficiency. The ramification is that the image size along with the imaging optics magnification dictates the field of view of the illumination module. Using the brightness equation, the angle space needed for the illumination module can be calculated from the FOV of the optics. This angle space allows for the determination of the minimum number of light sources of a given intensity necessary to provide the maximum flux (power) to the FOV. Optimizing the angle space utilized by the illumination and imaging systems can be accomplished by applying the brightness equation.

Figure 10:
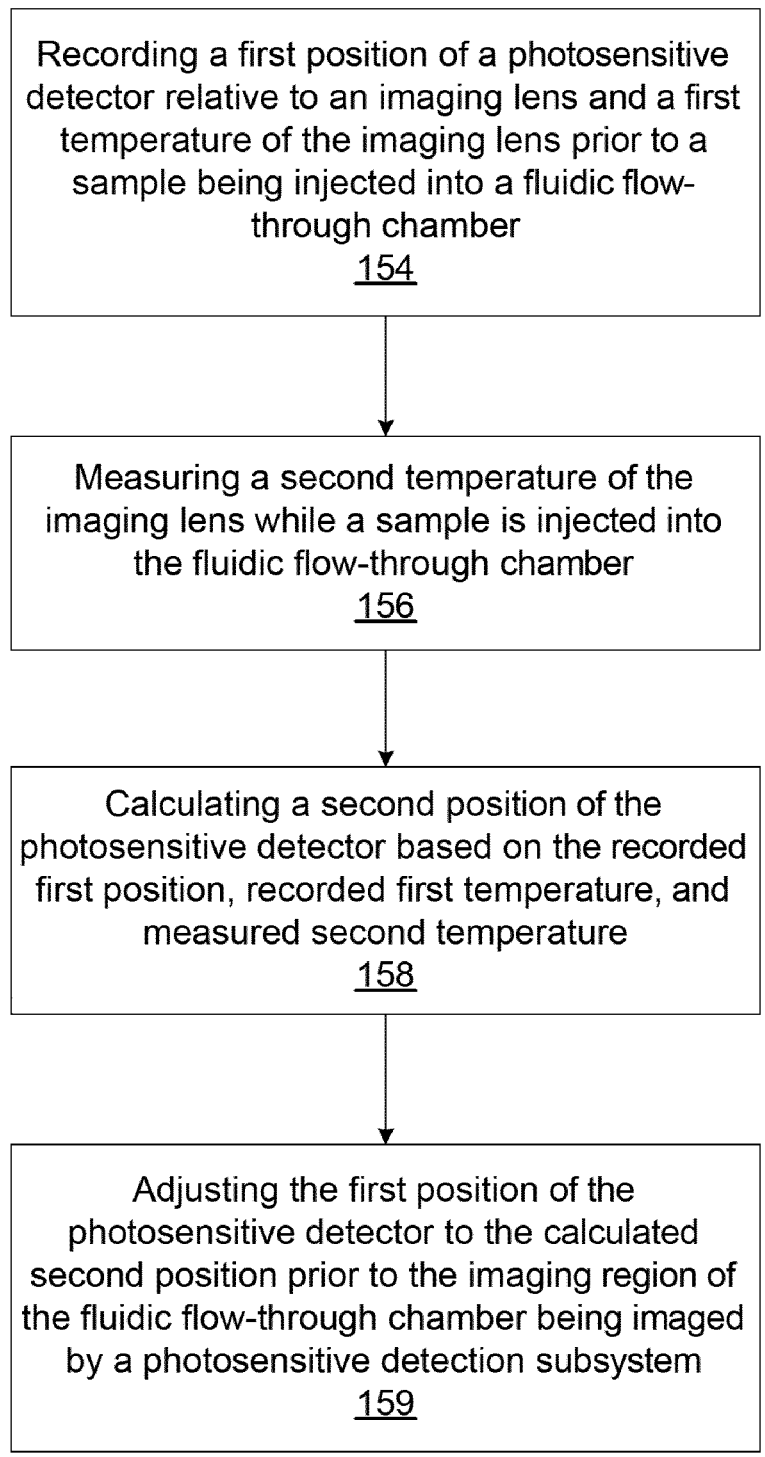
FIG. 10 is a flowchart of a method for regulating a focal position of a photosensitive detection subsystem relative to a temperature of an imaging lens.

During operation of the system described herein, environmental temperature changes (e.g., due to heat generated by the system) may cause the focal position of photosensitive detection subsystem to change. Therefore, in some embodiments, operation of the imaging system may include a method of regulating the focal position of the photosensitive detection subsystem based on operating temperature of the imaging lens. This can be achieved by use of a temperature sensor 142 described above in reference to FIG. 8. In addition, the calibration routine may be automated and, thus, the system described herein may include program instructions for performing the processes involved in the calibration routine. An exemplary calibration routine regulating the focal position of the photosensitive detection subsystem based relative to the temperature of the imaging lens is shown in FIG. 10. In particular, FIG. 10 denotes in block 154 that the calibration routine may include recording a first position of a photosensitive detector (e.g., photosensitive detector 144 in FIG. 8) relative to an imaging lens (e.g., imaging lens 140 in FIG. 8) and further recording a first temperature of the imaging lens prior to a sample being injected into a fluidic flow-through chamber (e.g., fluidic flow-through chamber 10 in FIG. 8) of the system. In addition, the calibration routine may include measuring a second temperature of the imaging lens while a sample is injected into the fluidic flow-through chamber as shown in block 156.

Based on the recorded first position, recorded first temperature, and the measured second temperature, a second position of the photosensitive detector may be calculated as denoted in block 158. The calculation is based on a predetermined formula relating the position of the photosensitive detector to the temperature of the imaging lens, which may generally vary among systems. An exemplary formula which may be used for the calculation in block 158 is:

$$F(2nd)=F(1st)+[T(2nd)-T(1st)]\times C$$

wherein:
F(2nd) is the calculated second position of the photosensitive detector
F(1st) is the first position of the photosensitive detector
T(2nd) is the measured second temperature of the imaging lens
T(1st) is the recorded first temperature of the imaging lens
C is a constant compensation factor predetermined for the system.

It is noted that the calculation used for block 158 is not limited to linear formulas. In particular, the calculation used for block 158 may include any mathematical formula, including but not limited to exponential and log-based equations. As noted above, the calculation used for block 158 may vary among systems. Thus, in some embodiments, the formula used for block 158 may include a compensation factor which is predetermined for the system, such as variable C in the equation noted above. The equation used for block 158, however, may alternatively not include such a factor.

As noted above, imaging lens 52 may be fixedly attached to a housing and, in some embodiments, imaging lens 52 and fluidic flow-through chamber 10 may be fixedly attached to the same housing and, thus, may be in fixed arrangement with respect to one another. Since imaging lens 52 is in a fixed position, it cannot be moved to adjust the focal position of the photosensitive detection subsystem. The photosensitive detector, however, is moveable relative to the imaging lens and, thus, the calibration routine outlined in FIG. 10 includes block 159 for adjusting the first position of the photosensitive detector to the calculated second position prior to the imaging region of the fluidic flow-through chamber being imaged by the photosensitive detection subsystem.

In some cases, the imaging system described herein may be configured to monitor the relationship between the position of photosensitive detector 144 and the temperature of imaging lens 140 to regulate a focal position of the photosensitive detection subsystem and adjust the formula used in reference to block 158 if the relationship changes. In particular, it is contemplated that characteristics and/or operation of some of the components within the system described herein may change over time and, in some embodiments, the changes may affect the relationship between the position of photosensitive detector 144 and the temperature of imaging lens 140 to regulate a focal position of the photosensitive detection subsystem. As such, the imaging system described herein may include an automated routine (i.e., via program instructions) for determining an optimum position of a photosensitive detector, recording and storing the optimum position and associated temperature of an imaging lens when such a position is determined, and adjusting a formula used by the system relating the position of the photosensitive detector to the temperature of the imaging lens based on the stored data. In general, such a routine may be performed during the entire "life" of the machine and, thus, such a routine is not limited to use when the system is fabricated. Rather, the routine may be conducted in the "field" when the imaging system is in possession of the consumer.

The determination of the optimum position of the photosensitive detector may include empirical iteration of different positions of the photosensitive detector and selecting the position generating the clearest image. The processes of determining, recording, and storing an optimum position and associated imaging lens temperature may be repeated such that a plurality of data is stored and may be referenced. The repetition of the processes may be conducted according to a preset periodic schedule or may be conducted upon command of a user of the imaging system. In either case, the automated routine may include analyzing all or a subset of the stored data to determine whether a relationship between the position of the photosensitive detector and the temperature of the imaging lens to regulate a focal position of the photosensitive detection subsystem has changed relative to a preset formula used by the system relating such parameters (i.e., the predetermined formula used in reference to block 158 of FIG. 10). The selection of data to be analyzed may be based on preset time parameters or may be selected by a user of the imaging system. Upon detecting a change in the relationship between the position of the photosensitive detector and the temperature of the imaging lens to regulate a focal position of the photosensitive detection subsystem, the automated routine may set a new formula by which to regulate the focal position of the photosensitive detection subsystem. Such a process may include refining the previous formula (e.g., adjusting constant compensation factor C in the exemplary equation noted above) or may include creating an entirely new formula solely based on the stored data.

For optimal performance of the imaging system described herein, it would be useful to be able to compare results obtained from different instruments and from different operating runs of the same instrument. However, a number of factors can affect the magnitude of the fluorescent signal detected by the imaging system. Some of these factors include luminous flux variances between individual light sources, such that at a given operating current, proportional variances occur in observed bead fluorescence (OBF) emitted from identical beads measured under otherwise identical operating conditions. In addition, environmental temperature variations can induce differences in light source output for a given current. Therefore, it would be useful if a light source current corresponding to a target OBF was identified for each fluorescence channel and a method of maintaining the target OBF over the system's operating temperature range was available.

Figure 11:
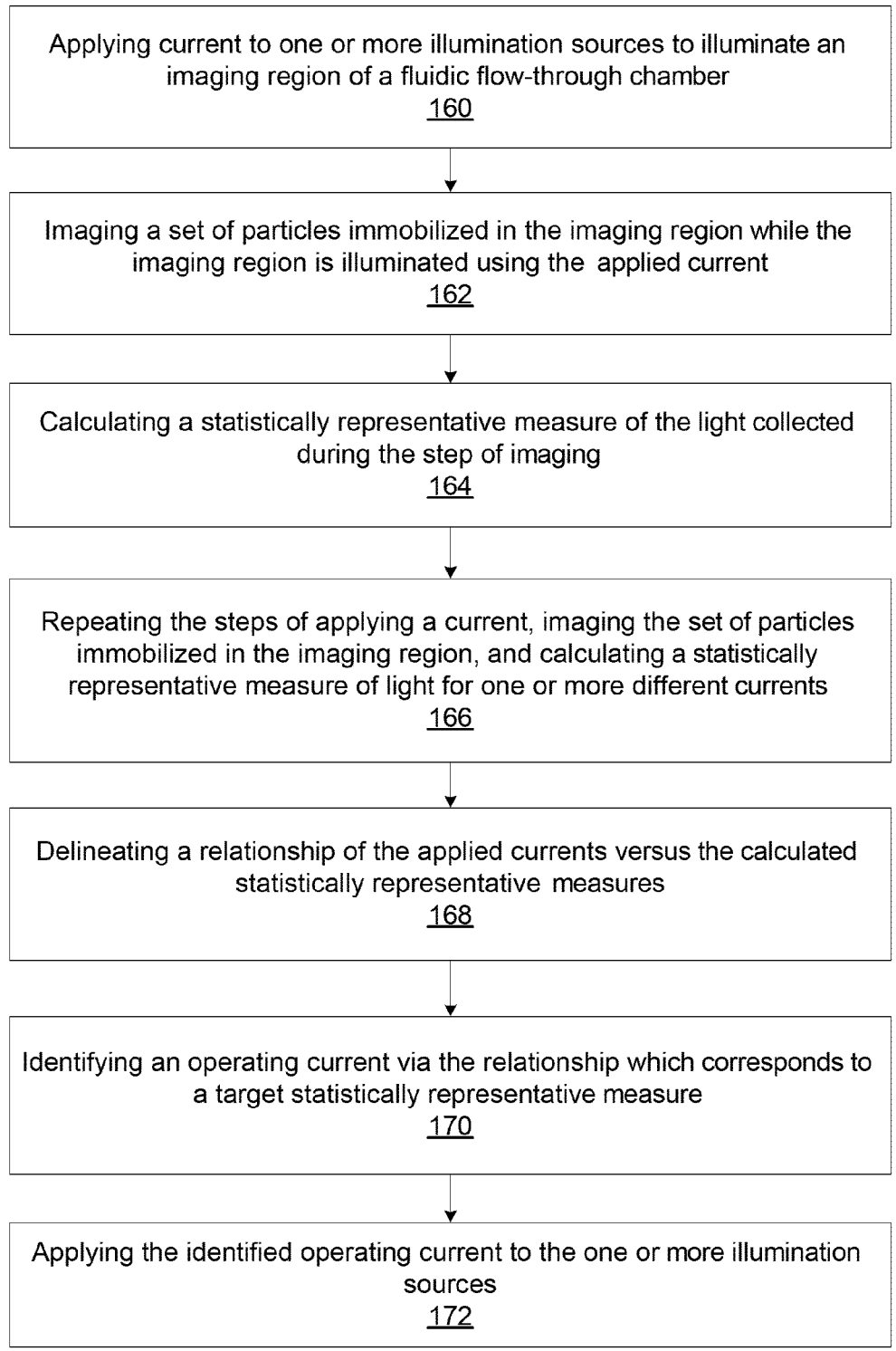
FIG. 11 is a flowchart of a method for identifying an operating current for one or more illumination sources of an illumination subsystem.

In some embodiments, operation of the imaging system described herein includes a calibration routine for identifying an operating current for one or more illumination sources of the imaging system. Such a calibration routine may be automated and, thus, the system described herein may include program instructions for performing the processes involved in the calibration routine. An exemplary calibration routine for identifying an operating current for one or more illumination sources of an illumination subsystem is shown in FIG. 11. In particular, FIG. 11 denotes in block 160 that a calibration routine may include applying current to one or more illumination sources (e.g., light sources 132 and 134 in FIG. 8) to illuminate an imaging region of a fluidic flow-through chamber (e.g., fluidic flow-through chamber 10 in FIG. 8). In addition, the routine includes imaging a set of particles immobilized in the imaging region while the imaging region is illuminated using the applied current and further calculating a statistically representative measure of the light collected during the step of imaging as noted in blocks 162 and 164, respectively. The statistically representative measure of light may include any statistical measure which is applicable for the collected light, including but not limited to the mean or median intensity of the collected light.

As noted in block 166, the steps of applying a current, imaging the set of particles immobilized in the imaging region, and calculating a statistically representative measure of light (i.e., the processes outlined in blocks 160-164) are repeated for one or more different currents. The number of times the processes are repeated may be preset or, in other words, the number of different currents evaluated may be preset. The different currents considered for the processes may, in some embodiments, include the smallest and largest currents of a current range selected to be used for the light sources. Subsequent to performing the processes outlined in blocks 160-164 the preset number of times, the calibration routine continues to block 168 to delineate a relationship of the applied currents versus the calculated statistically representative measures. Such a relationship may be any mathematical relationship, including but not limited to linear, exponential and log-based relationships. Using the defined relationship, an operating current may be identified which corresponds to a target statistically representative measure as denoted in block 170 and the identified operating current may then be applied to one or more of the illumination sources to analyze a sample as denoted in block 172.

To compensate for varying operating temperatures during normal instrument usage, integration times of the photosensitive detectors in the imaging device described herein may be adjusted to compensate for changes in light source output due to environmental operating temperature changes. It has been established that a linear relationship exists between integration time and observed brightness, as well as between light source brightness and temperature. Therefore, a proportional relationship between the integration time of photosensitive detectors and temperature can also be established. Accordingly, integration time of photosensitive detectors may be adjusted according to measured operating temperature changes to ensure optimal OBF is achieved regardless of operating temperature of the system. This can be achieved by use of a temperature sensor within the system. The temperature sensor may be arranged at any location within the system. In some embodiments, temperature sensor 142 arranged on the barrel of imaging lens 140 as described in reference to FIG. 8 may be used to regulate the integration time of the photosensitive detector/s. In other cases, however, the process to adjust the integration time of the photosensitive detectors may utilize a temperature sensor arranged at a different location within the system and, thus, the imaging system described herein may, in some embodiments, include two temperature sensors. In any case, a routine may be employed to regulate the integration time of a photosensitive detector based on the temperature of the system. The routine may be automated and, thus, the imaging system described herein may include program instructions for performing the processes involved in the routine.

Figure 12:
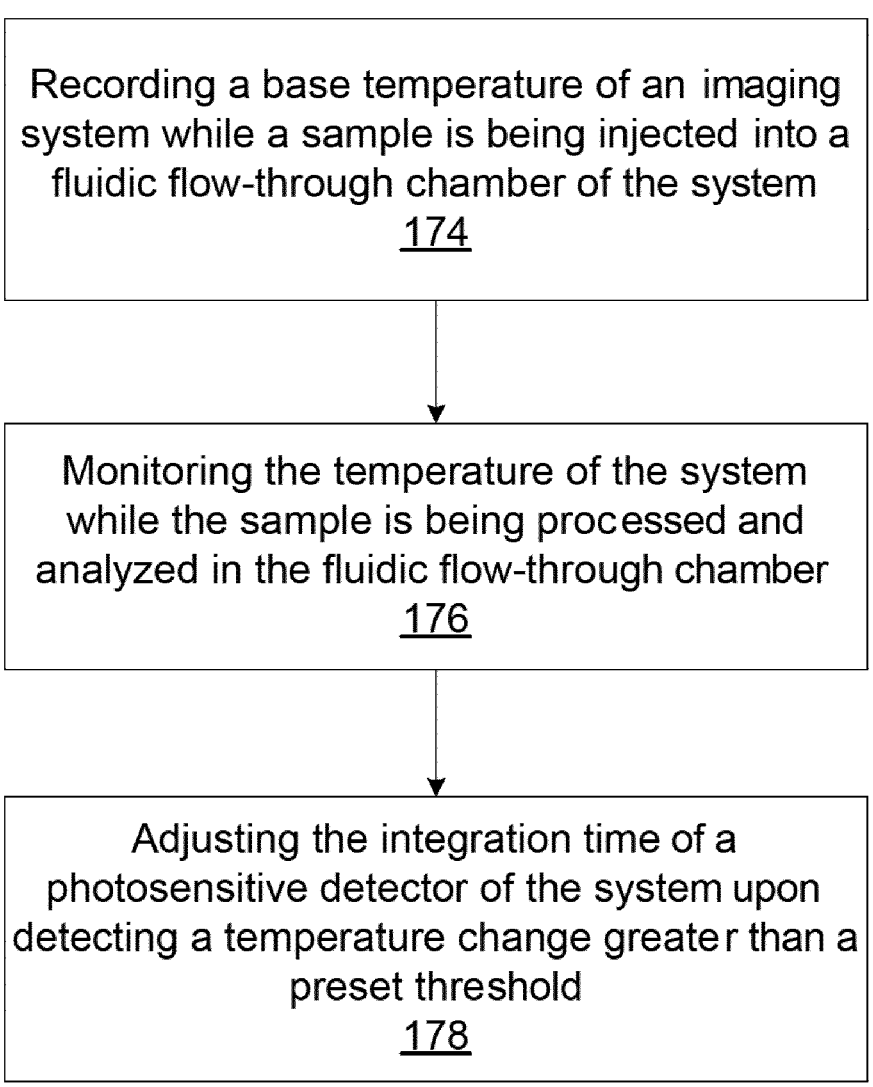
FIG. 12 is a flowchart of a method for regulating integration time of a photosensitive detector.

An exemplary routine for regulating integration time of a photosensitive detector within an imaging system is shown in FIG. 12. In particular, FIG. 12 denotes in block 174 recording a base temperature of an imaging system while a sample is being injected into a fluidic flow-through chamber (e.g., fluidic flow-through chamber 10 in FIG. 8) of the imaging system. The routine further includes monitoring the temperature of the imaging system while the sample is being processed and analyzed in the fluidic flow-through chamber as denoted in block 176. Upon detecting a temperature change greater than a preset threshold, the routine continues to block 178 to adjust the integration time of a photosensitive detector (e.g., photosensitive detector 144 in FIG. 8) within the imaging system. The preset threshold maybe any temperature delta, depending on the specifications of the system and the desired precision for regulating integration time of a photosensitive detector. In some embodiments, the process of adjusting the integration time of the photosensitive detector denoted in block 178 may include adjusting the integration time of the photosensitive detector by an amount proportional to the detected temperature change.

Figure 13:
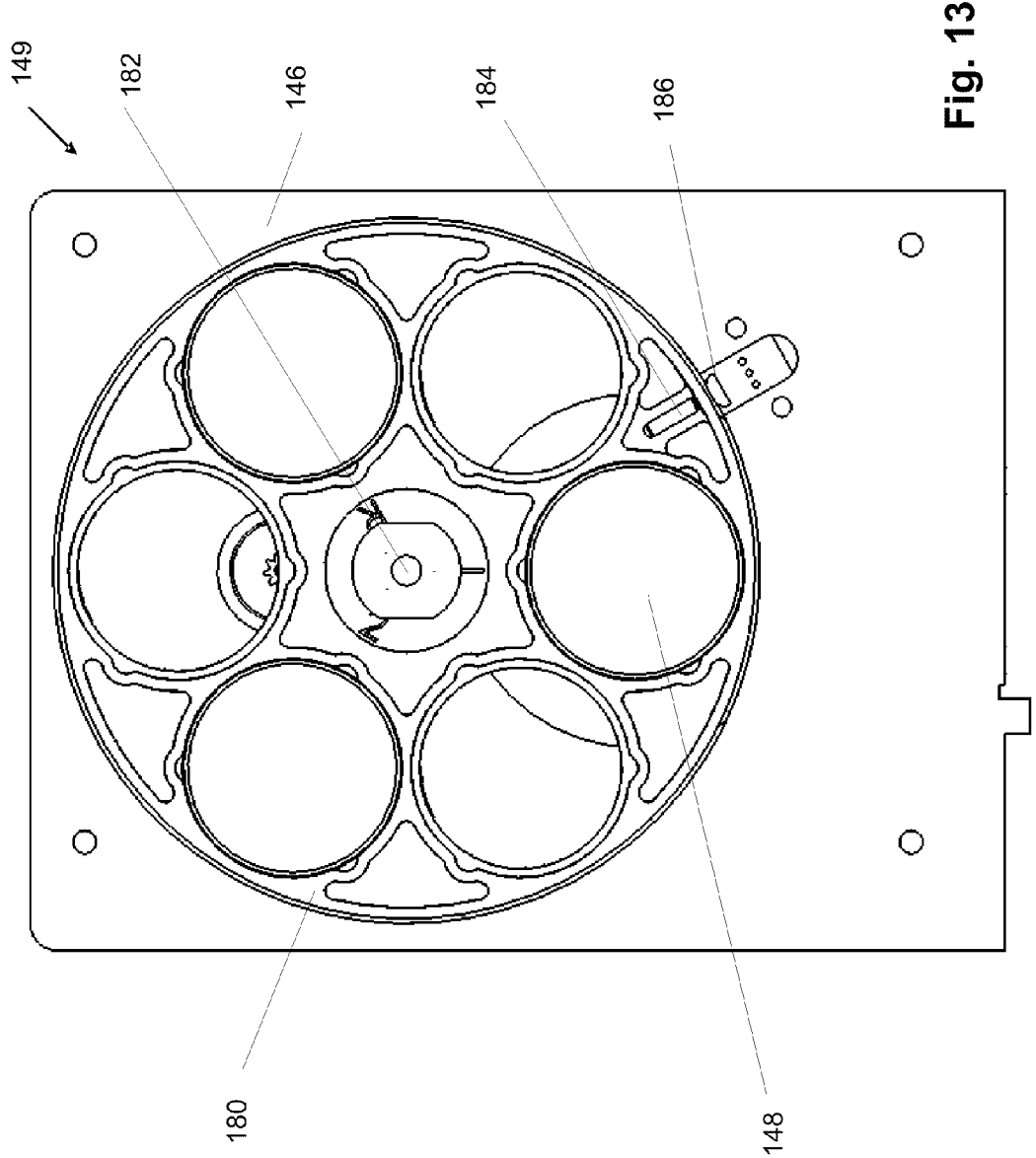
FIG. 13 illustrates an exemplary configuration of a filter wheel assembly for an imaging system.

As noted above in reference to FIG. 8, the photosensitive detector subsystem of the imaging system described herein may include filter wheel assembly 149 comprising multiple detection filters 148 disposed within substrate 146 and interposed between imaging lens 140 and photosensitive detector 144. The objective of filter wheel assembly 149 is to place different filters into the optical path of light exiting imaging lens 140 such that images at different wavelengths or different wavebands of interest may be acquired by photosensitive detector 144. An exemplary and more detailed configuration of filter wheel assembly 149 is illustrated in FIG. 13. In particular, filter wheel assembly 149 is shown in FIG. 13 including rotatable wheel 180 affixed to wheel mount 182 and plurality of filters 148 of different spectral characterization aligning the circumference of the rotatable wheel. In addition, FIG. 13 depicts filter wheel assembly 149 including filter wheel magnet 184 arranged on rotatable wheel 180 between two of filters 148 and further including magnetic field strength sensor 186 arranged on wheel mount 182. All of such components are arranged within or on substrate 146.

The number and selection of filters 148 used for imaging may generally vary among different sample analyses and, therefore, it may be advantageous to designate a "home position" of rotatable wheel 180 such that the address of each of filters 148 may be known for access (i.e., relative to the "home position"). In some cases, the approximate alignment of filter wheel magnet 184 and magnetic field strength sensor 186 may be designated as the "home position" of rotatable wheel 180. In particular, magnetic field strength sensor 186 may function to detect or measure the magnetic field provided by filter wheel magnet 184 and send out a discrete signal (high or low) when the field crosses a predetermined threshold, indicating whether the magnet is in the vicinity of the home position or not. As the filter wheel is turned, the magnet changes position relative to the magnetic field strength sensor and the magnetic field detected by the sensor varies accordingly. More specifically, magnetic field strength sensor 186 will detect relatively high magnetic fields when filter wheel magnet 184 is in the vicinity of the sensor and will detect lower magnetic fields when the magnet is farther away from the sensor. A particular magnetic field strength threshold may be used to indicate when filter wheel magnet 184 is coming in or leaving the vicinity of magnetic field strength sensor 186. However, such transitions points tend to occur at slightly different positions of the magnet relative to the sensor for each revolution of rotatable wheel 180. As such, it may be generally advantageous to perform a routine to calibrate a home position of rotatable wheel 180 prior to imaging a sample. As set forth in the exemplary calibration routine outlined in FIG. 14, by recording the position at which the transition points occur over multiple runs, it is possible to determine the most frequently measured "home" position of the rotatable wheel 180.

Figure 14:
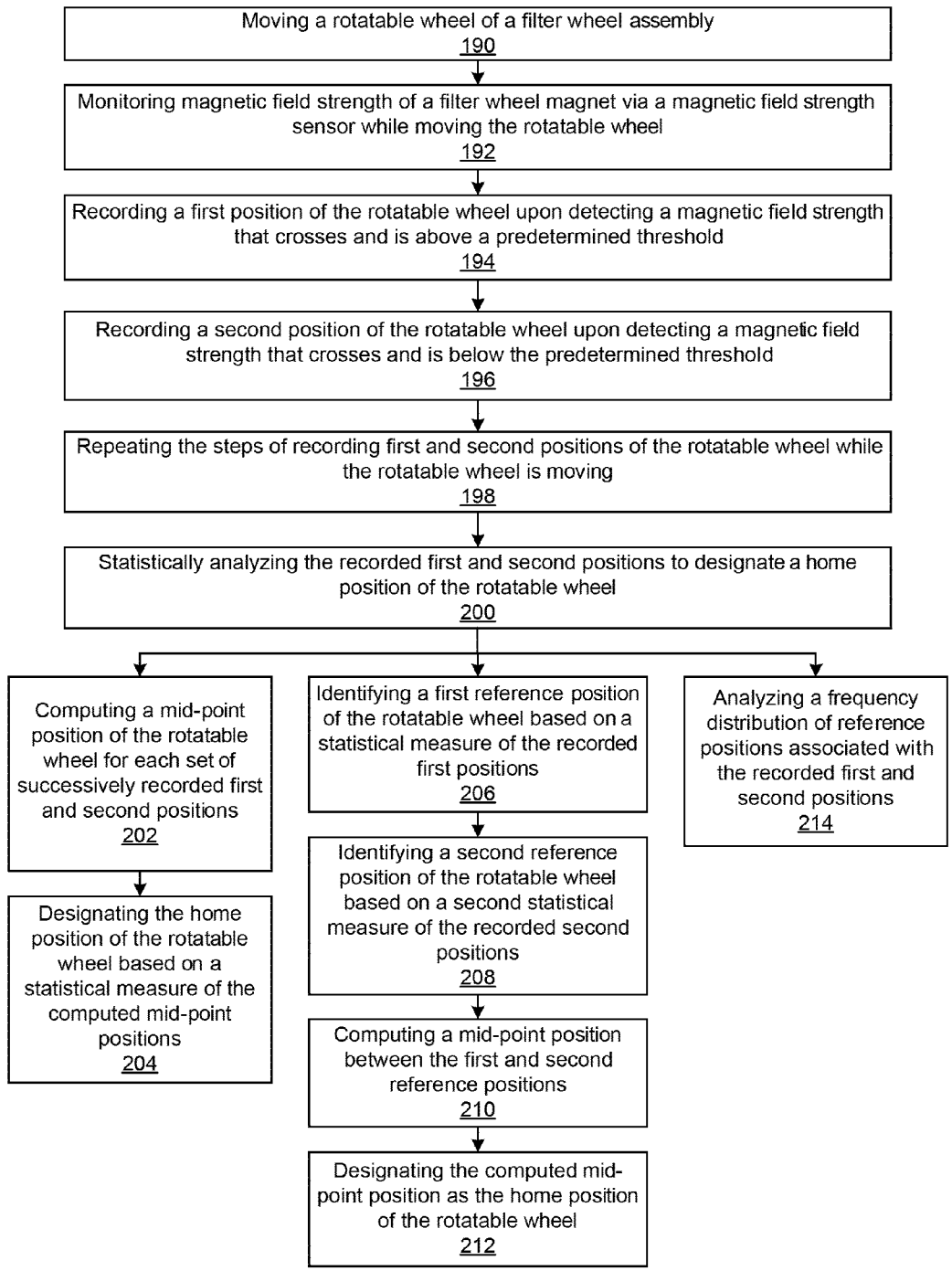
FIG. 14 is a flowchart for calibrating a home position of the rotatable wheel of the filter wheel assembly depicted in FIG. 13.

As respectively shown in blocks 190 and 192 of FIG. 14, a method for calibrating a home position of a rotatable wheel (e.g., rotatable wheel 180 in FIG. 13) of a filter wheel assembly may include moving the rotatable wheel and monitoring the magnetic field strength of a filter wheel magnet (e.g., filter wheel magnet 184 in FIG. 13) via a magnetic field strength sensor (e.g., magnetic field strength sensor 186 in FIG. 13) while moving the rotatable wheel. The process of moving the rotatable wheel denoted in block 190 may, in some embodiments, include rotating the rotatable wheel in full revolutions. In some cases, however, moving the rotatable wheel may include oscillating the rotatable wheel between transitions points of crossing the predetermined threshold referred to below in reference to blocks 194 and 196. In some embodiments, a combination of such scenarios may be used. For example, the calibration routine may start with rotating the rotatable wheel in full revolutions for a predetermined number of revolutions and then switch to oscillating the wheel.

In any case, the method may include recording a first position of the rotatable wheel upon detecting a magnetic field strength that crosses and is above a predetermined threshold and recording a second position of the rotatable wheel upon detecting a magnetic field strength that crosses and is below the predetermined threshold as respectively denoted in blocks 194 and 196. The predetermined threshold may generally depend on the specifications of the system as well as the desired precision for calibrating a home position of the rotatable wheel and, thus, may vary among different systems. The recorded first and second positions respectively represent the transition points when the filter wheel magnet is coming in the vicinity of the magnetic field strength sensor and when the magnet is moving away from the sensor. In particular, as the magnet approaches the magnetic field strength sensor while the rotatable wheel is moving, the strength of the magnetic field detected by the sensor will increase and will eventually cross and be above the predetermined threshold. In contrast, as the magnet moves farther away from the magnetic field strength sensor, the strength of the magnetic field detected by the sensor will decrease and will eventually cross and be below the predetermined threshold.

Continuing with the method outlined in FIG. 14, the processes of recording first and second positions of the rotatable wheel (i.e., the processes outlined in blocks 194 and 196) may be repeated while the rotatable wheel is moving as denoted in block 198. The number of times the processes are repeated may generally be preset and may be any number, depending on the desired precision of calibrating a home position of the rotatable wheel. Subsequent to recording a plurality of first and second positions, the recorded first and second positions are statistically analyzed to designate a home position of the rotatable wheel as shown in block 200. In general, the process of block 200 may be performed in a number of different manners, three of which are outlined in the branched structure extending from block 200 in FIG. 14. In particular, one manner for statistically analyzing the recorded first and second positions to designate a home position of the rotatable wheel is to compute a mid-point position of the rotatable wheel for each set of successively recorded first and second positions and designate the home position of the rotatable wheel based on a statistical measure of the computed mid-point positions as denoted in blocks 202 and 204, respectively. The statistical measure of the computed mid-point positions may include any statistical measure, including but not limited to the mean or median of the computed mid-point positions.

Yet, another manner to statistically analyze the recorded first and second positions to designate a home position of the rotatable wheel is to identify a first reference position of the rotatable wheel based on a statistical measure of the recorded first positions and identify a second reference position of the rotatable wheel based on a second statistical measure of the recorded second positions as denoted in blocks 206 and 208, respectively. The statistical measures of the recorded first and second positions may include any statistical measure, including but not limited to the mean or median of the recorded first and second positions. The process further includes blocks 210 and 212 in which a mid-point position between the first and second reference positions is computed and the computed mid-point position is designated as the home position of the rotatable wheel. In yet other embodiments, the process outlined in block 200 to statistically analyze the recorded first and second positions to designate a home position of the rotatable wheel may include analyzing a frequency distribution of reference positions associated with the recorded first and second positions as denoted in block 214 of FIG. 14. In any case, the routine outlined in FIG. 14 may be automated and, thus, the imaging system described herein may include program instructions for performing the processes involved in the routine.

The measurements described herein generally include image processing for analyzing one or more images of particles to determine one or more characteristics of the particles such as numerical values representing the magnitude of fluorescence emission of the particles at multiple detection wavelengths. Subsequent processing of the one or more characteristics of the particles such as using one or more of the numerical values to determine a token ID representing the multiplex subset to which the particles belong and/or a reporter value representing a presence and/or a quantity of analyte bound to the surface of the particles can be performed according to the methods described in U.S. Pat. Nos. 5,736,330 to Fulton, 5,981,180 to Chandler et al., 6,449,562 to Chandler et al., 6,524,793 to Chandler et al., 6,592,822 to Chandler, and 6,939,720 to Chandler et al., which are incorporated by reference as if fully set forth herein. In one example, techniques described in U.S. Pat. No. 5,981,180 to Chandler et al. may be used with the fluorescent measurements described herein in a multiplexing scheme in which the particles are classified into subsets for analysis of multiple analytes in a single sample.

It will be appreciated to those skilled in the art having the benefit of this disclosure that this invention is believed to provide systems and methods for performing measurements of one or more materials. Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as the presently preferred embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

What is claimed is:

1. A system for analyzing a fluidic assay, comprising:
a fluidic flow-through chamber;
a magnet and a mechanism for selectively positioning the magnet in proximity to an imaging region of the fluidic flow-through chamber;
an illumination subsystem configured to illuminate the imaging region of the fluidic flow-through chamber; and
a photosensitive detection subsystem configured to image the imaging region of the fluidic flow-through chamber when illuminated,
wherein the mechanism for selectively positioning the magnet comprises an actuator and a magnetic field strength sensor, and wherein the system comprises program instructions executable by a processor for calibrating a position of the magnet to which the mechanism is used to selectively move the magnet in proximity to the imaging region of the fluidic flow-through chamber, wherein the program instructions for calibrating the position of the magnet comprise program instructions for:
driving a motor to move the magnet toward the imaging region of the fluidic flowthrough chamber;
measuring output voltage of the magnetic field strength sensor while the magnet is moved toward the imaging region;
storing measured output voltages in a buffer;
terminating the motor upon detecting a negligible change in output voltage by the magnetic field strength sensor; and
designating one of the stored measured output voltages as a reference voltage for the mechanism to reach in selectively moving the magnet in proximity to the imaging region of the fluidic flow-through chamber.

2. A system for analyzing a fluidic assay, comprising:
a fluidic flow-through chamber;
a magnet and a mechanism for selectively positioning the magnet in proximity to an imaging region of the fluidic flow-through chamber;
an illumination subsystem configured to illuminate the imaging region of the fluidic flow-through chamber; and
a photosensitive detection subsystem configured to image the imaging region of the fluidic flow-through chamber when illuminated,
wherein the mechanism for selectively positioning the magnet comprises an actuator and a magnetic field strength sensor, and wherein the system comprises program instructions executable by a processor for commanding the mechanism to stop movement of the magnet relative to a reference voltage associated with a position in proximity to the imaging region of the fluidic flow-through chamber, wherein the program instructions for commanding the mechanism comprise program instructions for:
driving a motor of the mechanism to move the magnet toward the imaging region of the fluidic flow-through chamber;
monitoring output voltage of the magnetic field strength sensor while the magnet is moving; and
terminating the motor upon detecting that the output voltage equals the reference voltage.

3. The system of claim 2, wherein an interior back portion of the imaging region of the fluidic flow-through chamber comprises a roughened surface.

4. The system of claim 2, wherein the roughened surface comprises a surface roughness between approximately 0.6 microns root mean square and approximately 0.8 microns root mean square.

5. The system of claim 2, wherein the fluidic flow-through chamber comprises input and output channels for respectively receiving and dispensing a fluidic assay to and from the fluidic flow-through chamber, and wherein widths of the input and output channels are tapered relative to a width of the imaging region of the fluidic flow-through chamber.

6. The system of claim 2, wherein a back portion of the fluidic flow-through chamber corresponding to the imaging region of the fluidic flow-through chamber is coated with a coating configured to provide negligible reflectance and transmittance with respect to wavelengths of light emitted by the illumination subsystem.

7. The system of claim 2, wherein the mechanism for selectively positioning the magnet is configured to position the magnet such that a polarizing axis of the magnet is located downstream relative to a central point of the imaging region when the magnet is positioned in proximity to the imaging region.

8. The system of claim 7, wherein the mechanism for selectively positioning the magnet is configured to position the magnet such that a leading edge of the magnet is located downstream relative to a leading edge of the imaging region when the magnet is positioned in proximity to the imaging region.

9. The system of claim 2, wherein the mechanism for selectively positioning the magnet is configured to prevent the magnet from contacting the fluid flow-through chamber when the magnet is positioned in proximity to the imaging region.

10. A system for analyzing a fluidic assay, comprising:
a fluidic flow-through chamber;
a magnet and a mechanism for selectively positioning the magnet in proximity to an imaging region of the fluidic flow-through chamber;
an illumination subsystem configured to illuminate the imaging region of the fluidic flow-through chamber; and
a photosensitive detection subsystem configured to image the imaging region of the fluidic flow-through chamber when illuminated,
wherein the mechanism for selectively positioning the magnet comprises an actuator and a magnetic field strength sensor, and wherein the system comprises program instructions executable by a processor for commanding the mechanism to stop movement of the magnet relative to a reference voltage associated with a position in proximity to the imaging region of the fluidic flow-through chamber, wherein the program instructions for commanding the mechanism comprise program instructions for:
 driving a motor of the mechanism a predetermined number of steps to move the magnet toward the imaging region of the fluidic flow-through chamber;
 measuring output voltage of the magnetic field strength sensor after the motor has moved the predetermined number of steps;
 terminating the motor upon detecting a difference between the measured output voltage and the reference voltage less than a predetermined threshold; and
 effecting corrective action upon detecting a difference between the measured output voltage and the reference voltage greater than a predetermined threshold.

11. A system for analyzing a fluidic assay, comprising:
 a fluidic flow-through chamber;
 a magnet and a mechanism for selectively positioning the magnet in proximity to an imaging region of the fluidic flow-through chamber;
 an illumination subsystem configured to illuminate the imaging region of the fluidic flow-through chamber; and
 a photosensitive detection subsystem configured to image the imaging region of the fluidic flow-through chamber when illuminated,
 a storage vessel platform; a sample probe; and
 program instructions executable by a processor for calibrating a position of the sample probe relative to a well of a storage vessel arranged in the storage vessel platform, wherein the program instructions for calibrating the position of the sample probe comprise program instructions for:
  commanding a motor to move a set number of steps to drive the sample probe toward the well;
  monitoring capacitance between the sample probe and the storage vessel platform during or subsequent to the sample probe moving;
  monitoring the number of steps the motor drives the sample probe versus the set number of steps the motor is commanded to move;
  upon detecting a change in capacitance equal to or greater than a predetermined threshold or upon detecting the motor does not move the preset number of steps, recording the current position of the sample probe as a reference position;
  designating a target vertical position of the sample probe for extracting fluid assays from wells of the storage vessel based on the reference position; and
  repeating the steps of commanding the motor to move, monitoring capacitance, and monitoring the number of steps the motor moves until the target vertical position is designated or a predetermined number of iterations of the steps of commanding the motor to move, monitoring capacitance, and monitoring the number of steps the motor moves is conducted.

12. The system of claim 11, wherein the program instructions for designating the target vertical position of the sample probe comprise program instructions for designating the target vertical position at a position a set distance from the reference position farther from a bottom surface of the well.

13. The system of claim 11, wherein the program instructions for designating the target vertical position of the sample probe comprise program instructions for selectively designating the target vertical position different distances from the reference position based upon whether a capacitance equal to or greater than a predetermined threshold is detected or whether the motor not moving the set number of steps is detected.

14. The system of claim 11, wherein the program instructions for calibrating the position of the sample probe further comprise program instructions for:
 removing a drive current applied to the motor upon detecting the motor does not move the set number of steps; and
 pausing a set amount of time subsequent to removing the drive current and prior to recording the reference position.

15. A system for analyzing a fluidic assay, comprising:
 a fluidic flow-through chamber;
 a magnet and a mechanism for selectively positioning the magnet in proximity to an imaging region of the fluidic flow-through chamber;
 an illumination subsystem configured to illuminate the imaging region of the fluidic flow-through chamber; and
 a photosensitive detection subsystem configured to image the imaging region of the fluidic flow-through chamber when illuminated,
 wherein the photosensitive detection subsystem comprises: a photosensitive detector;
 an imaging lens fixedly attached to a housing to which the fluidic flow-through chamber is fixedly attached; and
 a temperature sensor arranged on a barrel of the imaging lens;
 wherein the system further comprises program instructions executable by a processor for regulating a focal position of the photosensitive detection subsystem relative to the temperature of the imaging lens, and wherein the program instructions for regulating the focal position of the photosensitive detection subsystem comprise program instructions for:
  recording a first position of the photosensitive detector relative to the imaging lens and a first temperature of the imaging lens prior to a sample being injected into the fluidic flow-through chamber;
  measuring a second temperature of the imaging lens while a sample is injected into the fluidic flow-through chamber;
  calculating a second position of the photosensitive detector based on the recorded first position, recorded first temperature, and measured second temperature; and
  adjusting the first position of the photosensitive detector to the calculated second position prior to the imaging region of the fluidic flow-through chamber being imaged by the photosensitive detection subsystem.

16. The system of claim 15, wherein the program instructions for calculating the second position of the photosensitive detector employ the equation of:

$$F(2nd)=F(1st)+[T(2nd)-T(1st)]\times C, \text{ wherein:}$$

F(2nd) is the calculated second position of the photosensitive detector;
F(1st) is the recorded first position of the photosensitive detector;
T(2nd) is the measured second temperature of the imaging lens;
T(1st) is the recorded first temperature of the imaging lens; and
C is a constant compensation factor predetermined for the system.

17. A system for analyzing a fluidic assay, comprising:
a fluidic flow-through chamber;
a magnet and a mechanism for selectively positioning the magnet in proximity to an imaging region of the fluidic flow-through chamber;
an illumination subsystem configured to illuminate the imaging region of the fluidic flow-through chamber; and
a photosensitive detection subsystem configured to image the imaging region of the fluidic flow-through chamber when illuminated,
wherein the photosensitive detection subsystem comprises:
an imaging lens;
a photosensitive detector; and
a filter wheel assembly interposed between the imaging lens and the photosensitive detector, wherein the filter wheel assembly comprises:
a rotatable wheel affixed to a wheel mount;
a plurality of filters of different spectral characterization aligning the circumference of the rotatable wheel;
a filter wheel magnet arranged on the rotatable wheel; and
a magnetic field strength sensor arranged on the wheel mount;
wherein the system further comprises program instructions executable by a processor for calibrating a home position of the rotatable wheel, and wherein the program instructions for calibrating the home position of the rotatable wheel comprise program instructions for:
moving the rotatable wheel;
monitoring magnetic field strength of the filter wheel magnet via the magnetic field strength sensor while moving the rotatable wheel;
recording a first position of the rotatable wheel upon detecting a magnetic field strength that crosses and is above a predetermined threshold;
recording a second position of the rotatable wheel upon detecting a magnetic field strength that crosses and is below the predetermined threshold;
repeating the steps of recording first and second positions of the rotatable wheel while the rotatable wheel is moving; and
statistically analyzing the recorded first and second positions to designate a home position of the rotatable wheel.

18. The system of claim 17, wherein the program instructions for statistically analyzing the recorded first and second positions comprise program instructions for:
computing a mid-point position of the rotatable wheel for each set of successively recorded first and second positions; and
designating the home position of the rotatable wheel based on a statistical measure of the computed mid-point positions.

19. The system of claim 17, wherein the program instructions for statistically analyzing the recorded first and second positions comprise program instructions for:
identifying a first reference position of the rotatable wheel based on a statistical measure of the recorded first positions;
identifying a second reference position of the rotatable wheel based on a second statistical measure of the recorded second positions; and
computing a mid-point position between the first and second reference positions; and
designating the computed mid-point position as the home position of the rotatable wheel.

20. The system of claim 17, wherein the program instructions for statistically analyzing the recorded first and second positions comprise program instructions for analyzing a frequency distribution of reference positions associated with the recorded first and second positions.

21. A system for analyzing a fluidic assay, comprising:
a fluidic flow-through chamber;
a magnet and a mechanism for selectively positioning the magnet in proximity to an imaging region of the fluidic flow-through chamber;
an illumination subsystem configured to illuminate the imaging region of the fluidic flow-through chamber; and
a photosensitive detection subsystem configured to image the imaging region of the fluidic flow-through chamber when illuminated, and
program instructions executable by a processor for identifying an operating current for one or more illumination sources of the illumination subsystem, wherein the program instructions for identifying the operating current comprise program instructions for:
applying current to the one or more illumination sources to illuminate the imaging region of the fluidic flow-through chamber;
imaging a set of particles immobilized in the imaging region while the imaging region is illuminated using the applied current;
calculating a statistically representative measure of the light collected during the step of Imaging;
repeating the steps of applying a current, imaging the set of particles immobilized in the imaging region, and calculating a statistically representative measure of light for one or more different currents;
delineating a relationship of the applied currents versus the calculated statistically representative measures;
identifying an operating current via the relationship which corresponds to a target statistically representative measure; and
applying the identified operating current to the one or more illumination sources of the illumination subsystem.

* * * * *